US012612391B2

(12) United States Patent
Elmaleh et al.

(10) Patent No.: US 12,612,391 B2
(45) Date of Patent: Apr. 28, 2026

(54) CROMOLYN DERIVATIVES AND USES THEREOF

(71) Applicant: The General Hospital Corporation, Boston, MA (US)

(72) Inventors: David R. Elmaleh, Newton, MA (US); Timothy M. Shoup, Franklin, MA (US)

(73) Assignee: The General Hospital Corporation, Boston, MA (US)

( * ) Notice: Subject to any disclaimer, the term of this patent is extended or adjusted under 35 U.S.C. 154(b) by 404 days.

(21) Appl. No.: 18/269,830

(22) PCT Filed: Dec. 27, 2021

(86) PCT No.: PCT/US2021/065200
§ 371 (c)(1),
(2) Date: Jun. 27, 2023

(87) PCT Pub. No.: WO2022/146914
PCT Pub. Date: Jul. 7, 2022

(65) Prior Publication Data
US 2024/0067635 A1 Feb. 29, 2024

Related U.S. Application Data

(60) Provisional application No. 63/131,135, filed on Dec. 28, 2020.

(51) Int. Cl.
*C07D 407/12* (2006.01)

(52) U.S. Cl.
CPC .................................. *C07D 407/12* (2013.01)

(58) Field of Classification Search
CPC ....... C07D 407/12; C07D 311/22; A61P 9/10; A61P 11/06; A61P 25/00; A61P 25/28; A61P 31/00; A61P 43/00; A61P 9/00
USPC .......................................................... 514/456
See application file for complete search history.

(56) References Cited

U.S. PATENT DOCUMENTS

| | | | |
|---|---|---|---|
| 3,419,578 | A | 12/1968 | Fitzmaurice et al. |
| 3,634,582 | A | 1/1972 | Hartley et al. |
| 3,686,412 | A | 8/1972 | Fitzmaurice et al. |
| 3,957,965 | A | 5/1976 | Hartley et al. |
| 4,120,285 | A | 10/1978 | Nugent |
| 4,405,598 | A | 9/1983 | Brown |
| 4,405,735 | A | 9/1983 | Wiezer et al. |
| 4,429,545 | A | 2/1984 | Steinberg |

(Continued)

FOREIGN PATENT DOCUMENTS

| | | | |
|---|---|---|---|
| CA | 2408793 | A1 | 12/2001 |
| CN | 101754746 | A | 6/2010 |

(Continued)

OTHER PUBLICATIONS

Abraham et al., "Mast cell-orchestrated immunity to pathogens," Nat Rev Immunol, 10: 440-452 (2010).

(Continued)

*Primary Examiner* — Taylor V Oh
(74) *Attorney, Agent, or Firm* — Foley Hoag LLP; Janine S. Ladislaw; Tatiana P. Headrick

(57) ABSTRACT

Described herein are compounds and methods of treating a disease or disorder, such as Alzheimer's disease, Parkinson's disease, Huntington's disease, ischemic stroke, and prion disease, comprising administering a therapeutically effective amount of a cromolyn ester.

18 Claims, 2 Drawing Sheets

(56) References Cited

U.S. PATENT DOCUMENTS

| | | | |
|---|---|---|---|
| 4,481,206 | A | 11/1984 | Spiegel et al. |
| 4,996,296 | A | 2/1991 | Pecht et al. |
| 5,376,386 | A | 12/1994 | Ganderton et al. |
| 5,567,720 | A | 10/1996 | Averback |
| 5,594,142 | A | 1/1997 | Gaa et al. |
| 5,655,523 | A | 8/1997 | Hodson et al. |
| 5,830,920 | A | 11/1998 | Chucholowski et al. |
| 5,904,937 | A | 5/1999 | Augello et al. |
| 6,168,776 | B1 | 1/2001 | Klunk et al. |
| 6,197,963 | B1 | 3/2001 | Hirschmann et al. |
| 6,262,108 | B1 | 7/2001 | Shirahase et al. |
| 6,309,623 | B1 | 10/2001 | Weers et al. |
| 6,696,039 | B2 | 2/2004 | Kung et al. |
| 6,911,466 | B2 | 6/2005 | Koo et al. |
| 6,946,116 | B2 | 9/2005 | Kung et al. |
| 6,972,127 | B2 | 12/2005 | Schenk |
| 7,160,559 | B1 | 1/2007 | McGee et al. |
| 7,186,401 | B2 | 3/2007 | Keller et al. |
| 7,858,803 | B2 | 12/2010 | Elmaleh et al. |
| 8,381,454 | B1 | 2/2013 | Robinson |
| 8,613,920 | B2 | 12/2013 | Lieberburg et al. |
| 8,617,517 | B2 | 12/2013 | Elmaleh et al. |
| 8,765,742 | B2 | 7/2014 | Hilfiker et al. |
| 9,283,230 | B2 | 3/2016 | Clunas et al. |
| 9,855,276 | B2 | 1/2018 | Elmaleh |
| 9,861,608 | B2 | 1/2018 | Elmaleh et al. |
| 9,913,847 | B2 | 3/2018 | Elmaleh |
| 9,918,992 | B2 | 3/2018 | Elmaleh |
| 9,925,282 | B2 | 3/2018 | Elmaleh et al. |
| 9,968,618 | B1 | 5/2018 | Elmaleh |
| 10,058,530 | B2 | 8/2018 | Elmaleh |
| 10,092,564 | B2 | 10/2018 | Moussy et al. |
| 10,188,757 | B2 | 1/2019 | Elmaleh |
| 10,238,628 | B2 | 3/2019 | Gerhart et al. |
| 10,245,331 | B2 | 4/2019 | Elmaleh |
| 10,251,961 | B2 | 4/2019 | Elmaleh |
| 10,398,704 | B2 | 9/2019 | Elmaleh |
| 10,406,164 | B2 | 9/2019 | Elmaleh |
| 10,413,551 | B2 | 9/2019 | Elmaleh |
| 10,525,005 | B2 | 1/2020 | Elmaleh |
| 10,561,612 | B2 | 2/2020 | Elmaleh et al. |
| 10,576,171 | B2 | 3/2020 | Elmaleh |
| 11,013,686 | B2 | 5/2021 | Elmaleh |
| 11,110,097 | B2 | 9/2021 | Elmaleh |
| 11,291,648 | B2 | 4/2022 | Elmaleh et al. |
| 11,666,669 | B2 | 6/2023 | Elmaleh |
| 11,679,095 | B2 | 6/2023 | Elmaleh et al. |
| 11,801,316 | B2 | 10/2023 | Elamaleh |
| 12,383,528 | B2 | 8/2025 | Elmaleh et al. |
| 12,458,622 | B2 | 11/2025 | Elmaleh et al. |
| 2002/0009491 | A1 | 1/2002 | Rothbard et al. |
| 2002/0016359 | A1 | 2/2002 | Hellberg et al. |
| 2002/0091100 | A1 | 7/2002 | Lezdey et al. |
| 2002/0107173 | A1 | 8/2002 | Friedhoff et al. |
| 2004/0176469 | A1 | 9/2004 | Thomas |
| 2004/0223918 | A1 | 11/2004 | Pham et al. |
| 2004/0259952 | A1 | 12/2004 | Abbas et al. |
| 2006/0051319 | A1 | 3/2006 | Yoo |
| 2006/0142241 | A1 | 6/2006 | Yoo |
| 2006/0159629 | A1 | 7/2006 | Tarara et al. |
| 2006/0240007 | A1 | 10/2006 | Sanders |
| 2006/0276455 | A1 | 12/2006 | Lindsberg et al. |
| 2007/0015813 | A1 | 1/2007 | Carter et al. |
| 2007/0053843 | A1 | 3/2007 | Dawson et al. |
| 2007/0071690 | A1 | 3/2007 | Mueller-Walz et al. |
| 2007/0086981 | A1 | 4/2007 | Meijer et al. |
| 2007/0093457 | A1 | 4/2007 | Arber et al. |
| 2007/0107173 | A1 | 5/2007 | Yamada |
| 2007/0178166 | A1 | 8/2007 | Bernstein et al. |
| 2007/0193577 | A1 | 8/2007 | Keller |
| 2007/0249644 | A1 | 10/2007 | Pearson et al. |
| 2007/0293538 | A1 | 12/2007 | Hobden |
| 2008/0021085 | A1 | 1/2008 | Koo et al. |
| 2009/0110679 | A1 | 4/2009 | Li et al. |
| 2009/0155256 | A1 | 6/2009 | Black et al. |
| 2010/0113613 | A1 | 5/2010 | McLaurin et al. |
| 2010/0143251 | A1 | 6/2010 | Tamagnan et al. |
| 2010/0173960 | A1 | 7/2010 | Cruz et al. |
| 2010/0234295 | A1 | 9/2010 | Chen |
| 2010/0236550 | A1 | 9/2010 | Zeng et al. |
| 2010/0266531 | A1 | 10/2010 | Hsieh et al. |
| 2010/0298389 | A1 | 11/2010 | Elmaleh et al. |
| 2011/0060138 | A1 | 3/2011 | Elmaleh et al. |
| 2011/0129530 | A1 | 6/2011 | Venkatesh et al. |
| 2011/0132434 | A1 | 6/2011 | Correia et al. |
| 2011/0262442 | A1 | 10/2011 | Hamilton et al. |
| 2012/0058049 | A1 | 3/2012 | Elmaleh et al. |
| 2012/0082727 | A1 | 4/2012 | Cocconi et al. |
| 2012/0118991 | A1 | 5/2012 | Keller et al. |
| 2012/0121656 | A1 | 5/2012 | Watson et al. |
| 2012/0134929 | A1 | 5/2012 | McGrath et al. |
| 2012/0165366 | A1 | 6/2012 | Ibrahim et al. |
| 2012/0175082 | A1 | 7/2012 | Kmetovicz et al. |
| 2012/0308613 | A1 | 12/2012 | Staniforth et al. |
| 2013/0197105 | A1 | 8/2013 | Pipkin et al. |
| 2014/0140927 | A1 | 5/2014 | Elmaleh et al. |
| 2014/0228304 | A1 | 8/2014 | Jones et al. |
| 2015/0224077 | A1 | 8/2015 | Gerhart et al. |
| 2015/0224078 | A1 | 8/2015 | Gerhart et al. |
| 2015/0274680 | A1 | 10/2015 | Ueda et al. |
| 2015/0283113 | A1 | 10/2015 | Elmaleh |
| 2016/0106704 | A1 | 4/2016 | Elmaleh et al. |
| 2016/0158150 | A1 | 6/2016 | Morton et al. |
| 2016/0166534 | A1 | 6/2016 | Elmaleh |
| 2016/0310503 | A1 | 10/2016 | Elmaleh |
| 2017/0290797 | A1 | 10/2017 | Elmaleh |
| 2018/0066039 | A1 | 3/2018 | Hyde-DeRuyscher et al. |
| 2018/0153803 | A1 | 6/2018 | Elmaleh |
| 2018/0169277 | A1 | 6/2018 | Elmaleh |
| 2018/0177789 | A1 | 6/2018 | Elmaleh |
| 2018/0177790 | A1 | 6/2018 | Elmaleh |
| 2018/0177791 | A1 | 6/2018 | Elmaleh |
| 2018/0193491 | A1 | 7/2018 | Elmaleh |
| 2018/0193492 | A1 | 7/2018 | Elmaleh |
| 2018/0344682 | A1 | 12/2018 | Elmaleh |
| 2019/0022006 | A1 | 1/2019 | Elmaleh et al. |
| 2019/0388568 | A1 | 12/2019 | Elmaleh |
| 2020/0022947 | A1 | 1/2020 | Elmaleh et al. |
| 2020/0078366 | A1 | 3/2020 | Elmaleh |
| 2020/0338040 | A1 | 10/2020 | Elmaleh |
| 2020/0383908 | A1 | 12/2020 | Elmaleh |
| 2021/0023010 | A1 | 1/2021 | Elmaleh et al. |
| 2021/0059977 | A1 | 3/2021 | Elmaleh |
| 2021/0085601 | A1 | 3/2021 | Elmaleh |
| 2022/0062222 | A1 | 3/2022 | Elmaleh et al. |
| 2022/0079914 | A1 | 3/2022 | Elmaleh et al. |
| 2022/0125753 | A1 | 4/2022 | Elmaleh |
| 2022/0193087 | A1 | 6/2022 | Elmaleh |
| 2022/0218652 | A1 | 7/2022 | Elmaleh et al. |
| 2023/0226017 | A1 | 7/2023 | Elmaleh |
| 2023/0248646 | A1 | 8/2023 | Elmaleh |
| 2023/0248650 | A1 | 8/2023 | Elmaleh et al. |
| 2024/0058480 | A1 | 2/2024 | Elmaleh |
| 2024/0067635 | A1 | 2/2024 | Elmaleh et al. |
| 2024/0082207 | A1 | 3/2024 | Elmaleh |

FOREIGN PATENT DOCUMENTS

| | | | |
|---|---|---|---|
| CN | 101848733 | A | 9/2010 |
| CN | 103347500 | A | 10/2013 |
| CN | 105377037 | A | 3/2016 |
| CN | 108164409 | A | 6/2018 |
| CN | 108403708 | A | 8/2018 |
| DE | 1543579 | | 6/2005 |
| EP | 1632242 | A2 | 3/2006 |
| EP | 2322163 | A1 | 5/2011 |
| EP | 2377860 | A1 | 10/2011 |
| EP | 2391618 | A2 | 12/2011 |
| EP | 2890788 | A1 | 7/2015 |
| EP | 2911664 | B1 | 5/2019 |
| GB | 1144906 | A | 3/1969 |
| GB | 1257162 | A | 12/1971 |
| JP | S56-043448 | B1 | 10/1981 |
| JP | H04505006 | A | 9/1992 |

(56) References Cited

FOREIGN PATENT DOCUMENTS

| | | | |
|---|---|---|---|
| JP | 2000-503866 | A | 4/2000 |
| JP | 2001-151673 | A | 6/2001 |
| JP | 2001-517691 | A | 10/2001 |
| JP | 2002-524107 | A | 8/2002 |
| JP | 2003-525842 | A | 9/2003 |
| JP | 2005-510535 | A | 4/2005 |
| JP | 2005-232171 | A | 9/2005 |
| JP | 2005-532091 | A | 10/2005 |
| JP | 2007-534693 | A | 11/2007 |
| JP | 2009-536918 | A | 10/2009 |
| JP | 2010-510254 | A | 4/2010 |
| JP | 2012-515712 | A | 7/2012 |
| JP | 2012-516356 | A | 7/2012 |
| WO | WO-1987/001115 | A1 | 2/1987 |
| WO | WO-90/09789 | A2 | 9/1990 |
| WO | WO-1997/026934 | A2 | 7/1997 |
| WO | WO-98/34596 | A2 | 8/1998 |
| WO | WO-1999/016422 | A1 | 4/1999 |
| WO | WO-1999/064095 | A2 | 12/1999 |
| WO | WO-02/28820 | A1 | 4/2002 |
| WO | WO-03/045331 | A2 | 6/2003 |
| WO | WO-2004/071532 | A1 | 8/2004 |
| WO | WO-2005/063732 | A1 | 7/2005 |
| WO | WO-2005/104712 | A2 | 11/2005 |
| WO | WO-2006/056492 | A1 | 6/2006 |
| WO | WO-2007/094718 | A1 | 8/2007 |
| WO | WO-2007/102059 | A1 | 9/2007 |
| WO | WO-2008/013799 | A2 | 1/2008 |
| WO | WO-2008/061373 | A1 | 5/2008 |
| WO | WO-2008/128981 | A1 | 10/2008 |
| WO | WO-2008/131298 | A2 | 10/2008 |
| WO | WO-2009/010770 | A2 | 1/2009 |
| WO | WO-2009/133128 | A1 | 11/2009 |
| WO | WO-2010/084767 | A1 | 7/2010 |
| WO | WO-2010/088455 | A2 | 8/2010 |
| WO | WO-2011/136754 | A1 | 11/2011 |
| WO | WO-2013/148366 | A1 | 10/2013 |
| WO | WO-2014/066318 | A1 | 5/2014 |
| WO | WO-2015/002703 | A1 | 1/2015 |
| WO | WO-2015/061397 | A1 | 4/2015 |
| WO | WO-2016/081466 | A1 | 5/2016 |
| WO | WO-2016/196401 | A1 | 12/2016 |
| WO | WO-2017/027387 | A1 | 2/2017 |
| WO | WO-2017/027402 | A1 | 2/2017 |
| WO | WO-2017/072335 | A1 | 5/2017 |
| WO | WO-2017/087962 | A1 | 5/2017 |
| WO | WO-2017/091644 | A1 | 6/2017 |
| WO | WO-2017/162884 | A1 | 9/2017 |
| WO | WO-2018/045217 | A1 | 3/2018 |
| WO | WO-2018/048989 | A1 | 3/2018 |
| WO | WO-2019/199776 | A1 | 10/2019 |
| WO | WO-2020/010049 | A1 | 1/2020 |
| WO | WO-2020/051322 | A1 | 3/2020 |
| WO | WO-2020/123449 | A1 | 6/2020 |
| WO | WO-2021/207060 | A1 | 10/2021 |
| WO | WO-2021/248022 | A1 | 12/2021 |
| WO | WO-2022/146914 | A1 | 7/2022 |

OTHER PUBLICATIONS

Aisen et al., "Effects of rofecoxib or naproxen vs placebo on Alzheimer disease progression: a randomized controlled trial," JAMA, 289(21):2819-2826 (2003).

Akiyama et al., "Inflammation and Alzheimer's Disease," Neurobiol Aging, 21(3): 383-421 (2000).

Alafuzoff et al., "Lower counts of astroglia and activated microglia in patients with Alzheimer's disease with regular use of non-steroidal anti-inflammatory drugs," J Alzheimers Dis, 2(1):37-46 (2000).

Albert et al., "Effects of age on the clinical pharmacokinetics of ibuprofen," Am J Med, 77(1, Part 1):47-50 (1984).

Albert et al., "Pharmacokinetics of ibuprofen," Am J Med, 77(1A):40-46 (1984).

Aloisi F. "Immune function of microglia". *Glia* (2001) 36,165-179.

Andreasen et al. "Sensitivity, specificity, and stability of CSF-tau in AD in a community-based patient sample," Neurology. (1999) 53: 1488-94 (19 pages).

Anonymous: "Facts about variant Creutzfeldt-Jakob disease", European Centre for Disease Prevention and Control, Jun. 26, 2017 (Jun. 26, 2017), pp. 1-10, XP093093988, European Centre for Disease Prevention and Control website.

Arnáiz et al., "Neuropsychological features of mild cognitive impairment and preclinical Alzheimer's disease," Acta Neurol Scand Suppl. (2003) 179: 34-41.

Aswania et al., "Relative bioavailability of sodium cromoglycate to the lung following inhalation, using urinary excretion," J Clin Pharmacol, 47:613-618 (1999).

Baig et al., "Use of Peptides for the Management of Alzheimer's Disease: Diagnosis and Inhibition," Frontiers in Aging Neuroscience, 10: 1-6 (2018).

Banati, R. B. et al., "Cytotoxicity of microglia". *Glia* (1993) 7, 111-118.

Bannwarth et al., "Stereoselective disposition of ibuprofen enantiomers in human cerebrospinal fluid.," Br J Clin Pharmacol, 40(3):266-269 (1995).

Barone, F.C. et al., "Tumor necrosis factor-$\alpha$: a mediator of focal ischemic brain injury". *Stroke* (1997) 28, 1233-1244.

Basek et al., "Efficacy of an Isotonic Small Droplet Size Nebulized DSCG on Asthma Control in Children," Acta Paediatrica, 99(Suppl 462):115 (2010).

Beach et al., "Cromolyn sodium toxicity studies in primates," Toxicol Appl Pharmacol, 57(3):367-400 (1981).

Beigel JH, et al. "Remdesivir for the treatment of Covid-19—preliminary report," The New England Journal of Medicine: 1-12 (2020).

Berge et al., "Pharmaceutical salts," J Pharm Sci, 66(1):1-19 (1977).

Blennow K., "Biomarkers in Alzheimer's disease drug development," Nat Med. (2010) 16: 1218-22.

Bodor et al., "Improved delivery through biological membranes VII. Dermal delivery of cromoglycic acid (cromolyn) via its prodrugs," International Journal of Pharmaceutics, 7(1):63-75 (1980).

Bona, E. et al., "Chemokine and inflammatory cell response to hypoxia-ischemia in immature rats". *Pediatr. Res.* (1999) 45, 500-509.

Bot et al., "Perivascular mast cells promote atherogenesis and induce plaque destabilization in apolipoprotein E-deficient mice," Circulation, 115(19):2516-2525 (2007).

Brazier et al., "Pharmacokinetics of cromolyn and ibuprofen in healthy elderly volunteers", *Clinical drug investigation* 37: 1025-1034 (2017).

Breitner et al., "Extended results of the Alzheimer's disease anti-inflammatory prevention trial," Alzheimers Dement, 7(4):402-411 (2011).

Breitner, "Alzheimer disease: The changing view," Annals Neurol, 49(3):418-419 (2001).

Broe et al., "Anti-inflammatory drugs protect against Alzheimer disease at low doses," Arch Neurol, 57:1586-1591 (2000).

Buchhave et al., "Cerebrospinal fluid levels of $\beta$-amyloid 1-42, but not of tau, are fully changed already 5 to 10 years before the onset of Alzheimer dementia," Arch Gen Psychiatry. (2012) 69: 98-106.

Bulic et al., "Tau protein and tau aggregation inhibitors," Neuropharmacology, 59: 276-289 (2010).

Butovsky et al., "Identification of a unique TGF-$\beta$-dependent molecular and functional signature in microglia," Nat Neurosci, 17(3): 131-143 (2014).

Byron et al., "Selection and Validation of Cascade Impactor Test Methods," Respiratory Drug Delivery IX, 1: 169-178 (2004).

Bäckman et al., "Multiple Cognitive Deficits During the Transition to Alzheimer's Disease," Journal of Internal Medicine, (2004) 256(3): 195-204.

Cacabelos, "Donepezil in Alzheimer's disease: From conventional trials to pharmacogenetics," Neuropsychiatric Disease and Treatment 3(3):303-333 (2007).

Cairns et al., "Synthesis and Structure-Activity Relationships of Disodium Cromoglycate and Some Related Compounds," Journal of Medicinal Chemistry, 15(6):583-589 (1972).

(56) References Cited

OTHER PUBLICATIONS

Carlesimo et al., "Memory Deficits in Alzheimer's Patients: A Comprehensive Review," Neuropsychol Rev. (1992) 3(2): 119-169.
Certificate of Analysis for Lactohale LH 201, Alpha-Lactose Monohydrate EP and USP, Full Release (DFE Pharma); Jan. 18, 2016.
Chen et al., "Current experimental therapy for Alzheimer's Disease," Curr Neuropharmacol, 5(2): 127-134 (2007).
Cherry et al., "Neuroinflammation and M2 microglia: the good, the bad, and the inflamed," J Neuroinflammation, 11(98): 1-15 (2014).
Choi et al., "A three-dimensional human neural cell culture model of Alzheimer's disease," Nature, 515: 274-278 (2014).
Chow et al., "Investigation of Electrostatic Behavior of a Lactose Carrier for Dry Powder Inhalers," Pharmaceutical Research, 25(12): 2822-2834 (2008).
ClinicalTrials.gov. Phase 1 Study of ALZT-OP1 Combination Therapy in Normal Healthy Volunteers. Sponsor: AZTherapies, Inc. Identifier: NCT02482324. Retrieved Apr. 9, 2020 from: http://clinicaltrials.gov/ct/show/NCT02482324?order=1.
ClinicalTrials.gov. Safety and Efficacy of ALZT-OP1a as Adjuvant Treatment in Subjects With Post-Ischemic Stroke Cognitive Impairment (PSCI). Sponsor: AZTherapies, Inc. Identifier: NCT03202147. Retrieved Feb. 6, 2020, 2020 from: https://clinicaltrials.gov/ct2/show/NCT03202147?term=cromolyn&draw=3&rank=11.
ClinicalTrials.gov. Safety and Efficacy Study of ALZT-OP1 in Subjects With Evidence of Early Alzheimer's Disease (COGNITE). Sponsor: AZTherapies, Inc. Identifier: NCT02547818. Retrieved Apr. 9, 2020 from: https://clinicaltrials.gov/ct2/show/study/NCT02547818?term=AZTherapies&draw=2&rank=1.
ClinicalTrials.gov. Treatment of Acute Stroke With Cromolyn(Single Dose). Sponsor: Wolfson Medical Center. Identifier: NCT01175525. Retrieved Feb. 6, 2020 from: https://clinicaltrials.gov/ct2/show/NCT01175525.
Cole et al., "Mechanisms of action of non-steroidal anti-inflammatory drugs for the prevention of Alzheimer's disease," CNS Neurol Disord Drug Targets, 9(2):140-148 (2010).
Conti et al., "Induction of pro-inflammatory cytokines (IL-1 and IL-6) and lung inflammation by Coronavirus-19 (COVI-19 or SARS-CoV-2): anti-inflammatory strategies," J Biol Regul Homeost Agents, 34(2): 327-331 (2020).
Cowell, R.M. et al., "Hypoxic-ischemic injury induces macrophage inflammatory protein-1alpha expression in immature rat brain," *Stroke* (2002) 33,795-801.
Cox et al., "Disodium Cromoglycate (FPL 670) ('Intal'*): A Specific Inhibitor of Reaginic Antibody-Antigen Mechanisms," Nature, 216: 1328-1329 (1967).
Cruz M.P., "Edaravone (Radicava): A novel neuroprotective agent for the treatment of amyotrophic lateral sclerosis," P&T. (2018) 43(1):25-28.
Cummings, "Alzheimer's Disease," N Engl J Med, 351(1):56-67 (2004).
Das et al., "Importance of particle size and shape on the tensile strength distribution and de-agglomeration of cohesive powders," Powder Technology, 249: 297-303 (2013).
Davies, "Clinical pharmacokinetics of ibuprofen. The first 30 years," Clin Pharmacokinet, 34(2):101-154 (1998).
Deiana et al., "Methylthioninium Chloride Versus Rivastigmine and Their Co-Administration Efficacy in Reversing Scopolamine-Induced Cognitive Deficits in a Pharmacological Mouse Model of Alzheimer's Disease," Alzheimer's and Dementia, 4(4, Supplement): T499 (2009).
Dello Russo et al., "The human microglial HMC3 cell line: where do we stand? A systematic literature review," J Neuroinflammation, 15: 259 (24 pages) (2018).
Denes, A. et al., "Proliferating resident microglia after focal cerebral ischaemia in mice," *J. Cereb. Blood. Flow. Metab.* (2007) 27, 1941-1953.
Desmond, D.W. et al., "Frequency and clinical determinants of dementia after ischemic stroke." *Neurology* (2000), 54, 1124-1131.
Dickson et al., "Diffuse Lewy body disease," Acta Neuropathol (Berl), 75: 8-15 (1987).
Doody et al., "Donepezil treatment of patients with MCI: a 48-week randomized, placebo-controlled trial," Neurology, 72(18):1555-1581 (2009).
Du et al., "Role of Microglia in Neurological Disorders and Their Potentials as a Therapeutic Target," Mol Neurobiol, 54: 7567-7584 (2017).
Dubbelaar et al., "The Kaleidoscope of Microglial Phenotypes," Front Immunol, 9: 1753 (2018).
Dunbar et al., "Dispersion and Characterization of Pharmaceutical Dry Powder Aerosols," Kona, 16:7-45 (1998).
Elmaleh, D.R. et al., "Evaluation of F-18 Radiolabeled Cromolyn as a Potential Aβ Polymerization Inhibitor and PET Tracer". Poster at *Human Amyloid Image* (*HAI*) *Conference*, Miami, Florida, Jan. 2014.
EPAR (European Public Assessment Report) Seebri Breezhaler: Retrieved online at <http://www.ema.europa.eu/ema/index.jsp?curl=pages/medicines/human/medicines/002430/human_med_001580.jsp&mid=WC0b01ac058001d124>: 6 pages (2012).
Etminan et al., "Effect of non-steroidal anti-inflammatory drugs on risk of Alzheimer's disease: systematic review and meta-analysis of observational studies," Brit Med J, 327:128-131 (2003).
European Search Report for EP Application No. 13848340 dated Feb. 11, 2016.
European Search Report for European Application No. 14819448.3 dated Feb. 2, 2017.
Extended European Search Report for EP Application No. 10736439.0 issued Jun. 12, 2012.
Extended European Search Report for EP Application No. 16867341.6 mailed Jun. 13, 2019.
Extended European Search Report for EP Application No. 17934303 mailed Aug. 13, 2021.
Extended European Search Report for EP Application No. 19786110.7 dated Mar. 7, 2022.
Extended European Search Report for EP Application No. 19830061.8 dated Mar. 11, 2022.
Extended European Search Report for EP Application No. 19857627.4 dated Aug. 8, 2022.
Extended European Search Report for EP Application No. 19895399.4 dated Oct. 27, 2022.
Extended European Search Report for EP Application No. EP 16869210 dated Sep. 19, 2019.
Extended European Search Report for EP Application No. EP 17847576 dated Jun. 30, 2020.
Extended European Search Report for EP Application No. EP 17918310 mailed Mar. 12, 2021.
Extended European Search Report for EP Application No. EP 19166810 dated Sep. 23, 2019.
Extended European Search Report for EP Application No. EP 19172666 dated Jan. 10, 2020.
Extended European Search Report, EP 14855211.0, dated May 29, 2017.
Fiala, M. et al., "IL-17A is increased in the serum and in spinal cord CD8 and mast cells of ALS patients," *J Neuroinflammation*. (2010) 7:76.
Findeis et al., "Design and testing of inhibitors of fibril formation," Methods Enzymol, 309:476-488 (1999).
Findeis et al., "Modified-peptide inhibitors of amyloid β-peptide polymerization," Biochemistry, 38(21):6791-6800 (1999).
Francesch et al., "Chronic inflammation (inflammaging) and its potential contribution to age-associated diseases," J Gerontol A Biol Sci Med Sci, 69(S1): S4-9 (2014).
Franzius, D., et al., "Non-specific effects of calcium entry antagonists in mast cells," *Pflugers Arch.* (1994) 428(5-6):433-438.
Gadani et al., "IL-4 in the brain: a cytokine to remember," J Immunol, 189(9): 4213-4219 (2012).
Galimberti et al., "Disease-modifying treatments for Alzheimer's disease," Ther Adv Neurol Disord, 4(4):203-216 (2011).
Garmise, "Novel Dry Powder Preparations of Whole Inactivated Influenza Virus for Nasal Vaccination," Dissertation, University of North Carolina at Chapel Hill (2007).

(56) References Cited

OTHER PUBLICATIONS

Garringer et al., "Modeling familial British and Danish dementia", Brain Struct Funct 214(2-3):235-244 (2010).
Gasparini et al., "Non-steroidal anti-inflammatory drugs (NSAIDs) in Alzheimer's disease: old and new mechanisms of action," J Neurochem, 91(3):521-536 (2004).
Ghasemi. M. and Brown. R.H. Jr. "Genetics of amyotrophic lateral sclerosis," *Cold Spring Harb. Perspect. Med.* (2018) 8(5).
Gilani et al., "Influence of Formulation Variables and Inhalation Device on the Deposition Profiles of Cromolyn Sodium Dry Powder Aerosols," Daru 12(3):123-130 (2004).
Gilead Announces Approval of Veklury (remdesivir) in Japan for Patients With Severe COVID-19. The press release of Gilead Sciences. May 7, 2020. URL: < https://www.gilead.com/news-and-press/press-room/press-releases/2020/5/gilead-announces-approval-of-veklury-remdesivir-in-japan-for-patients-with-severe-covid19>. Retrieved on Jul. 14, 2021.
Gomperts et al., "Imaging amyloid deposition in Lewy body disease," Neurology, 71 (12): 903-910 (2008).
Gorelick, P.B. et al., "Vascular Contributions to Cognitive Impairment and Dementia, A Statement for Healthcare Professionals from the American Heart Association/American Stroke Association," *Stroke* (2011) 42, 2672-2713.
Gosselin et al., "An environment-dependent transcriptional network specifies human microglia identity," Science, 356: eaal3222 (2017).
Granucci et al., "Cromolyn sodium delays disease onset and is neuroprotective in the SOD1G93A Mouse Model of amyotrophic lateral sclerosis," Sci Rep, 9: 17728 (17 pages) (2019).
Granucci et al., "Inducible IL-2 production by dendritic cells revealed by global gene expression analysis," Nat Immunol, 2(9): 882-888 (2001).
Greenhalgh et al., "Immune cell regulation of glia during CNS injury and disease," Nat Rev Neurosci, 21: 139-152 (2020).
Grenier et al., "Three-dimensional modeling of human neurodegeneration: brain organoids coming of age," Mol Psychiatry, 25: 254-274 (2020).
Griffin, "What causes Alzheimer's?" The Scientist, 25:36-40 (2011).
Grundman et al., "Mild cognitive impairment can be distinguished from Alzheimer disease and normal aging for clinical trials," Arch. Neurol. (2004) 61(1): 59-66.
Guchardi et al., "Influence of fine lactose and magnesium stearate on low dose dry powder inhaler formulations," International Journal of Pharmaceutics 348:10-17 (2008).
Gudesblatt et al., "Hexosaminidase A activity and amyotrophic lateral sclerosis," Muscle and Nerve, II: 227-230 (1988).
Guo et al., "Comparison of Delivery Characteristics from a Combination Metered-Dose Inhaler Using the Andersen Cascade Impactor and the Next Generation Pharmaceutical Impactor," J Pharm Sci, 97(8): 3321-3334 (2008).
Guo, J. et al., "Evaluating the levels of CSF and serum factors in ALS," *Brain Behav.* (2017) 7:e00637.
Gwin et al., "Cromolyn sodium in the treatment of asthma associated with aspirin hypersensitivity and nasal polyps," Chest, 72(2):148-153 (1977).
Haass et al., "Soluble protein oligomers in neurodegeneration: lessons from the Alzheimer's amyloid [beta]-peptide," Nat Rev Mol Cell Biol, 8(2):101-112 (2007).
Hallenbeck, J.M. "The many faces of tumor necrosis factor in stroke". *Nat Med* (2002) 8, 1363-1368.
Han et al., "The therapeutic effects of sodium cromoglycate against influenza A virus H5N1 in mice," Influenza and Other Respiratory Viruses, 10(1): 57-66 (2015).
Hashimoto et al., "Apolipoprotein E, especially apolipoprotein E4, increases the oligomerization of amyloid β peptide," J Neurosci, 32(43):15181-15192 (2012).
He et al., "Progress of Inhaled Devices for Asthma," Journal of Applied Clinical Pediatrics, 22(4):309-311 (2007).
Hemonnot et al., "Microglia in Alzheimer Disease: Well-Known Targets and New Opportunities," Front Aging Neurosci, 11:233(20 pages) (2019).
Heneka et al., "Acute treatment with the PPARγ agonist pioglitazone and ibuprofen reduces glial inflammation and Aβ1-42 levels in APPV717I transgenic mice," Brain, 128:1442-1453 (2005).
Hensley, "Neuroinflammation in Alzheimer's Disease: Mechanisms, Pathologic Consequences, and Potential for Therapeutic Manipulation," J Alzheimers Dis, 21(1):1-14 (2010).
Hirouchi, "Current status and perspectives on the development of therapeutic agents for Alzheimer's disease," Nihon Yakurigaku Zasshi, 123(6):421-427 (2004).
Hofman et al., "Atherosclerosis, apolipoprotein E, and prevalence of dementia and Alzheimer's disease in the Rotterdam Study," Lancet 349: pp. 151-154 (1997).
Holian et al., "Mechanistic aspects of cromolyn sodium action on the alveolar macrophage: inhibition of stimulation by soluble agonists," Agents Actions, 33: 318-325 (1991).
Hoozemans et al., "Soothing the inflamed brain: effect of non-steroidal anti-inflammatory drugs on Alzheimer's disease pathology," CNS Neurol Disord Drug Targets, 10(1):57-67 (2011).
Hopperton et al., "Markers of microglia in post-mortem brain samples from patients with Alzheimer's disease: a systematic review," Mol Psychiatry, 23: 177-198 (2018).
Hori et al., "A Food and Drug Administration-approved asthma therapeutic agent impacts amyloid beta in the brain in a transgenic model of Alzheimer disease," J Biol Chem, 290(4): 1966-1978 (2015).
Hu et al., "Increased peripheral blood inflammatory cytokine levels in amyotrophic lateral sclerosis: a meta-analysis study," Scientific Reports, 7: Article No. 9094 (2017).
Huang et al., "Acute stress induces cardiac mast cell activation and histamine release, effects that are increased in Apolipoprotein E knockout mice.," Cardiovasc Res, 55(1):150-160 (2002).
Huang et al., "Stress-induced interleukin-6 release in mice is mast cell-dependent and more pronounced in Apolipoprotein E knockout mice," Cardiovasc Res, 59(1):241-249 (2003).
Ihle-Hansen, H. et al., "Incidence and subtypes of MCI and dementia 1 year after first-ever stroke in patients without pre-existing cognitive impairment," *Dement. Geriatr. Cogn. Disord.* (2011) 32, 401-407.
Ilieva, H., et al., "Non-cell autonomous toxicity in neurodegenerative disorders: ALS and beyond," *J. Cell Biol.* (2009) 187(6):761-772.
Imbimbo et al., "Are NSAIDs useful to treat Alzheimer's disease or mild cognitive impairment?," Front Aging Neurosci, 2(19):1-14 (2010).
Imbimbo, "An update on the efficacy of non-steroidal anti-inflammatory drugs in Alzheimer's disease," Expert Opinion on Investigational Drugs, 2009; 18(8), pp. 1147-1168.
InnoPharmalabs, "Particle Size Distribution", Apr. 9, 2013 (Apr, 9, 2013).
Intal Approval Package, Center for Drug Evaluation and Research, application 75-175, pp. 1-5 (Dec. 12, 1997).
Intal® Nebulizer Solution (Label 2016): Retrieved online at <http://labeling.pfizer.com/ShowLabeling.aspx?id=833>: 4 pages (2016).
International Preliminary Report on Patentability for International Application No. PCT/US2019/040247 dated Jan. 14, 2021.
International Search Report and Written Opinion for International Application No. PCT/US16/63143 mailed Feb. 6, 2017.
International Search Report and Written Opinion for International Application No. PCT/US16/63462 mailed Feb. 1, 2017.
International Search Report and Written Opinion for International Application No. PCT/US17/65727 mailed Feb. 12, 2018.
International Search Report and Written Opinion for International Application No. PCT/US19/49733 dated Jan. 13, 2020.
International Search Report and Written Opinion for International Application No. PCT/US2010/022495 dated Nov. 10, 2010.
International Search Report and Written Opinion for International Application No. PCT/US2014/061694 dated Jan. 2, 2015.
International Search Report and Written Opinion for International Application No. PCT/US2017/049702 dated Dec. 26, 2017.
International Search Report and Written Opinion for International Application No. PCT/US2019/026521 dated Jun. 14, 2019.
International Search Report and Written Opinion for International Application No. PCT/US2019/040247 dated Sep. 20, 2019.

(56) References Cited

OTHER PUBLICATIONS

International Search Report and Written Opinion for International Application No. PCT/US2021/025746 mailed Jun. 17, 2021.
International Search Report and Written Opinion for International Application No. PCT/US2021/035936 dated Jul. 22, 2021.
International Search Report and Written Opinion for International Application No. PCT/US2021/065200 dated Mar. 24, 2022.
International Search Report and Written Opinion for International Application No. PCT/US19/65384 dated Mar. 31, 2020.
International Search Report for International Application No. PCT/US14/39118 dated Sep. 18, 2014.
International Search Report for International Application No. PCT/US2013/066069 mailed Mar. 13, 2014.
Jellinger, K.A., "Alzheimer disease and cerebrovascular pathology: an update". *J. Neural. Transm.* (2002) 109, 813-836.
Jin et al., "Mast cells are early responders after hypoxia-ischemia in immature rat brain," Stroke, 40(9):3107-3112 (2009).
Jin, R. et al., "Inflammatory mechanisms in ischemic stroke: role of inflammatory cells," *J Leukoc Biol* (2010) 87, 779-789.
Jin, Y. et al., "Mast cell stabilization limits hypoxic-ischemic brain damage in the immature rat". *Dev Neurosci.* (2007) 29, 373-384.
Jurga et al., "Overview of General and Discriminating Markers of Differential Microglia Phenotypes," Front Cell Neurosci, 14: 198 (18 pages) (2020).
Kamiya., "Characteristics and problems of cascade impactors in the evaluation of inhaled preparations," Journal of Pharmaceutical Science and Technology, Japan, 65(4): English Machine Translation (5 pages)(2005).
Karadsheh, "Rapid response to: Covid-19: what treatments are being investigated?" BMJ (4 pages) (2020).
Karran et al., "The amyloid cascade hypothesis for Alzheimer's disease: an appraisal for the development of therapeutics," Nat Rev, 10(9):698-712 (2011).
Kaur et al., "Drug Therapy in Stroke: From Preclinical to Clinical Studies," Pharmacology, 92:324-334 (2013).
Kay et al., "Disodium cromoglycate inhibits activation of human inflammatory cells in vitro," J Allergy Clin Immunol, 80(1): 1-8 (1987).
Keizman D. et al. Low-grade systemic inflammation in patients with amyotrophic lateral sclerosis. *Acta Neurol Scand.* (2009) 119:383-389.
Keller et al., "Have inadequate delivery systems hampered the clinical success of inhaled disodium cromoglycate? Time for reconsideration," Exp Opin Drug Deliv, 8(1):1-17 (2011).
Kelley et al., "The molecular role of mast cells in atherosclerotic cardiovascular disease," Mol Med Today, 6:304-308 (2000).
Kilpatrick et al., "Cromolyn inhibits assembly of the NADPH oxidase and superoxide anion generation by human neutrophils," *The Journal of Immunology*, 154(7): 3429-3436 (1995).
Knowles, "Donepezil in Alzheimer's disease: an evidence-based review of its impact on clinical and economic outcomes," Core Evid, 1(3):195-219 (2006).
Kohman et al., "Neurogenesis, inflammation and behavior," Brain Behav Immun, 27C:22-32 (2013).
Kondo et al., "iPSC-Based Compound Screening and In Vitro Trials Identify a Synergistic Anti-amyloid β Combination for Alzheimer's Disease," Cell Rep, 21: 2304-2312 (2017).
Koo et al., "Amyloid diseases: Abnormal protein aggregation in neurodegeneration, " PNAS, 96:9989-9990 (1999).
Kotilinek et al., "Cyclooxygenase-2 inhibition improves amyloid-β-mediated suppression of memory and synaptic plasticity," Brain, 131(3):651-664 (2008).
Koudstaal et al., "Secondary Stroke Prevention in Atrial Fibrillation: Indications, Risks, and Benefits," J Thromb Thrombolys, 7(1):61-65 (1999).
Krstic et al., "Deciphering the mechanism underlying late-onset Alzheimer disease," Nat Rev Neurol, 9:25-34(2013).
Krueger, M. et al., "Blood-brain barrier breakdown involves four distinct stages of vascular damage in various models of experimental focal cerebral ischemia," *J. Cereb. Blood Flow Metab.* (2015), 35, 292-303.
Kuhle, J. et al., Increased levels of inflammatory chemokines in amyotrophic lateral sclerosis, *Eur J Neurol.* (2009) 16:771-774.
Kumon et al., "Application and Mechanism of Inhalation Profile Improvement of DPI Formulations by Mechanofusion with Magnesium Stearate," Chemical and Pharmaceutical Bulletin, 56(5): 617-625 (2008).
Kwong et al., "Comparison of Nebulized Particle Size Distribution with Malvern Laser Diffraction Analyzer Versus Andersen Cascade Impactor and Low-Flow Marple Personal Cascade Impactor," J Aerosol Med, 13(4): 303-314 (2000).
Lalancette-Hébert, M et al., "Selective ablation of proliferating microglial cells exacerbates ischemic injury in the brain," *J Neurosci* (2007) 27, 2596-2605.
Lanari, et al., "Cerebrospinal fluid biomarkers and prediction of conversion in patients with mild cognitive impairment: 4-year follow-up in a routine clinical setting," Scientific World Journal. (2009) 9: 961-6.
Lanz et al., "The γ-Secretase Inhibitor N-[N-(3,5-Difluorophenacetyl)-L-alanyl]-S-phenylglycine t-butyl Ester Reduces Aβ Levels in Vivo in Plasma and Cerebrospinal Fluid in Young (Plaque-Free) and Aged (Plaque-Bearing) Tg2576 Mice," The Journal of Pharmacology and Experimental Therapeutics, 305(3):864-871 (2003).
Lasiene, J and Yamanaka, K., "Glial cells in amyotrophic lateral sclerosis," *Neurol Res Int.* (2011) 2011: Article ID 718987.
Lee, P.H. et al., "Circulating beta amyloid protein is elevated in patients with acute ischemic stroke". *J. Neural. Transm.* (*Vienna*). (2005) 112, 1371-9.
Lehman, L.L. and Rivkin, M.J., "Perinatal arterial ischemic stroke: Presentation, risk factors, evaluation, and outcome". *Pediatr. Neurol.* (2014) 51, 760-768.
Lewis et al., "Quantification of Alzheimer pathology in aging and dementia: age-related accumulation of amyloid-β (42) peptide in vascular dementia," Neuropathology and Applied Neurobiology, 32(2): 103-118 (2006).
Li et al., "TREM2 regulates innate immunity in Alzheimer's disease," J Neuroinflammation, 15: 107 (7 pages) (2018).
Libby, "Inflammation in atherosclerosis," Nature, 420(6917):868-874 (2002).
Lim et al., "Ibuprofen Suppresses Plaque Pathology and Inflammation in a Mouse Model of Alzheimer's Disease," The Journal of Neuroscience 20(15):5709-5714 (2000).
Liu et al., "Elevated Levels of IFN-γ in CSF and Serum of Patients with Amyotrophic Lateral Sclerosis," Plos One, 10(9): 11 pages (2015).
Liu, Y.H et al., "Aβ is predictive for short-term neurological deficits after acute ischemic stroke". *Neurotox Res.* (2015) 27, 292-299.
Lobo-Silva et al., "Balancing the immune response in the brain: IL-10 and its regulation," J Neuroinflammation, 13: 297 (10 pages) (2016).
Loeb et al., "A randomized, controlled trial of doxycycline and rifampin for patients with Alzheimer's disease," J Am Geriatr Soc, 52(3): 381-7 (2004).
Mackenzie et al., "Nonsteroidal anti-inflammatory drug use and Alzheimer-type pathology in aging," Neurology, 50(4):986-990 (1998).
Madureira, S. et al., "Dementia and cognitive impairment three months after stroke". *Eur J Neurol* (2001) 8, 621-627.
Mandel, "CERE-110, an adeno-associated virus-based gene delivery vector expressing human nerve growth factor for the treatment of Alzheimer's disease," Curr Opin Mol Ther, 12(2): 240-247 (2010).
Marinkovic et al., "Evolution of Intracerebral Hemorrhage after Intravenous Tpa: Reversal of Harmful Effects with Mast Cell Stabilization," J Cerebr Blood F Met, 34(1):176-181 (2014).
Mash et al., "Loss of M2 muscarine receptors in the cerebral cortex in Alzheimer's disease and experimental cholinergic denervation," Science, 228(4703):1115-1117 (1985).

(56) References Cited

OTHER PUBLICATIONS

Material Safety Data Sheet Cromolyn Sodium: Retrieved online at<https://www.biobasic.com/amfilerating/file/download/file_id/24861/http://www.alli.wnyric.org/District/Documents/msds/files/cjx/cjxjy.html>: 5 pages (2017).
Mattson, M.P. et al., "Cellular signaling roles of TGFβ, TNF α and β APP in brain injury responses and Alzheimer's disease". *Brain Res. Brain Res. Rev.* (1997) 23, 47-61.
McArthur et al., "Annexin A1: a central player in the anti-inflammatory and neuroprotective role of microglia," J Immunol 185: 6317-6328 (2010).
McGeer et al. "Targeting microglia for the treatment of Alzheimer's disease," Expert Opin Ther Targets 19: 497-506 (2015).
McKittrick et al., "Mast Cells Promote Blood Brain Barrier Breakdown and Neutrophil Infiltration in a Mouse Model of Focal Cerebral Ischemia," J Cerebr Blood F Met, 35(4):638-647 (2015).
McLaurin et al., "Cyclohexanehexol inhibitors of AB aggregation prevent and reverse Alzheimer phenotype in a mouse model," Nat Med, 12(7):801-808 (2006).
Mitchell et al., "Aerodynamic Particle Size Analysis of Aerosols from Pressurized Metered-Dose Inhalers: Comparison of Andersen 8-Stage Cascade Impactor, Next Generation Pharmaceutical Impactor, and Model 3321 Aerodynamic Particle Sizer Aerosol Spectrometer," AAPS PharmSciTech, 4(4): Article 54 (2003).
Mohammed et al., "Effect of Sampling Volume on Dry Powder Inhaler (DPI)-Emitted Aerosol Aerodynamic Particle Size Distributions (APSDs) Measured by the Next-Generation Pharmaceutical Impactor (NGI) and the Andersen Eight-Stage Cascade Impactor (ACI)," APPS PharmSciTech, 13(3): 875-882 (2012).
Monge-Argilés et al. "Biomarkers of Alzheimer's disease in the cerebrospinal fluid of Spanish patients with mild cognitive impairment," Neurochem Res. (2011) 36: 986-993.
Mor et al., "Mast cells and atherosclerosis," Israel Med Assoc J, 3:216-221 (2001).
Moreau C. et al. Elevated IL-6 and TNF-alpha levels in patients with ALS: inflammation or hypoxia. Neurology. (2005) 65:1958-1960.
Morihara et al., "Ibuprofen Suppresses Interleukin-1β Induction of Pro-Amyloidogenic $\alpha_1$-Antichymotrypsin to Ameliorate β-Amyloid (ABβ) Pathology in Alzheimer's Models," Neuropsychopharmacology 30:1111-1120 (2005).
Moss et al., "The absorption and clearance of disodium cromoglycate from the lung in rat, rabbit, and monkey," Toxicol Appl Pharmacol, 17(3):699-707 (1970).
Mrak et al., Common Inflammatory Mechanisms in Lewy Body Disease and Alzheimer Disease, J Neuropathol Exp Neurol, 66(8): 683-686 (2007).
Murphy, "Cromolyn sodium: basic mechanisms and clinical usage," Pediatric Asthma, Allergy, and Immunology, 2(4):237-254 (1988).
Müller et al., "Fluorine in Pharmaceuticals: Looking Beyond Intuition," Science, 317: 1881 (2007).
Nagamoto-Combs et al., "Microglial phenotype is regulated by activity of the transcription factor, NFAT (nuclear factor of activated T cells)," J Neurosci, 30(28): 9641-9646 (2010).
Nagoshi, N. et al., "Riluzole as a neuroprotective drug for spinal cord injury: from bench to bedside," *Molecules.* (2015) 20(5):7775-7789.
Nakajima, K. and Kohsaka, S., "Microglia: activation and their significance in the central nervous system," *J Biochem* (2001) 130, 169-175.
Neale et al., "The pharmacokinetics of sodium cromoglycate in man after intravenous and inhalation administration," Br J Clin Pharmacol, 22:373-382 (1986).
Netzer et al., "The actual role of sodium cromoglycate in the treatment of asthma—a critical review," Sleep Breath, 16:1027-1032 (2012).
Newman et al., "Evolution of dry powder inhaler design, formulation, and performance," Respiratory Medicine, 96(5): 293-304 (2002).
Newman et al., "Therapeutic Aerosols 1—Physical and Practical Considerations," Thorax, 38(12): 881-886 (1983).
Nihashi, T. et al., "Expression and distribution of beta amyloid precursor protein and beta amyloid peptide in reactive astrocytes after transient middle cerebral artery occlusion," *Acta Neurochir (Wien)*. (2001) 143, 287-295.
Noristani et al., "RNA-Seq Analysis of Microglia Reveals Time-Dependent Activation of Specific Genetic Programs following Spinal Cord Injury," Front Mol Neurosci, 10: 90 (16 pages) (2017).
Notice of Allowance and Fees Due for U.S. Appl. No. 14/059,924 dated Aug. 18, 2017.
Notice of Allowance and Fees Due for U.S. Appl. No. 14/059,924 dated Jan. 12, 2018.
Notice of Allowance and Fees Due for U.S. Appl. No. 15/360,451 dated Apr. 24, 2018.
Notice of Allowance and Fees Due for U.S. Appl. No. 15/838,753 dated Mar. 21, 2019.
Notice of Allowance and Fees Due for U.S. Appl. No. 15/895,312 dated Apr. 6, 2018.
Notice of Allowance and Fees Due for U.S. Appl. No. 15/902,491 dated Apr. 19, 2019.
Notice of Allowance and Fees Due for U.S. Appl. No. 15/916,740 dated Apr. 26, 2019.
Notice of Allowance and Fees Due for U.S. Appl. No. 15/830,980, "Methods for Delivering Cromolyn," mailed Aug. 6, 2019.
Notice of Allowance and Fees Due for U.S. Appl. No. 15/838,753, "Powdered Formulations of Cromolyn Sodium and Ibuprofen," mailed Oct. 2, 2019.
Notice of Allowance and Fees Due for U.S. Appl. No. 15/902,486, "Combination Therapies for the Treatment of Alzheimer's Disease and Related Disorders," mailed Jul. 22, 2019.
Notice of Allowance and Fees Due for U.S. Appl. No. 15/902,491, "Combination Therapies for the Treatment of Alzheimer's Disease and Related Disorders," mailed Jul. 9, 2019.
Notice of Allowance and Fees Due for U.S. Appl. No. 15/902,498, "Combination Therapies for the Treatment of Alzheimer's Disease and Related Disorders," mailed Jul. 10, 2019.
Notice of Allowance for U.S. Appl. No. 15/031,098 mailed Dec. 13, 2018.
Nys, G.M. et al., "Restrictions of the Mini-Mental State Examination in acute stroke." *Arch Clin Neuropsychol* (2005) 20, 623-629.
Obici et al., "AA amyloidosis: basic knowledge, unmet needs and future treatments," Swiss Medical Weekly, 142:w13580 (2012).
Omer et al., "Comparison between the next generation impactor and the twin glass impinge as model pulmonary drug delivery devices," Zanco J. Med. Sci., 23(1): 74-80 (2019).
Onderdijk et al., "IL-4 Downregulates IL-1B and IL-6 and Induces GATA3 in Psoriatic Epidermal Cells: Route of Action of a Th2 Cytokine," J Immunol, 195: 1744-1752 (2015).
Ono et al., "Push-pull benzothiazole derivatives as probes for detecting β-amyloid plaques in Alzheimer's brains," Bioorg Med Chem, 17(18):7002-7007 (2009).
Onodera et al., "Appropriate Administration Setting and Efficacy Evaluation in Clinical Trials (Phase I to III Clinical Trials) for the Development of New Drugs," Science & Technology Co., Ltd., 1st Edition, p. 100-101.
Orr et al., "A Brief Overview of Tauopathy: Causes, Consequences, and Therapeutic Strategies," Trends in Pharmacological Sciences, 38(7): 637-648 (2017).
Package Insert Intal® (Label 2003): Retrieved online at http://www.accessdata.fda.gov/drugsatfda_docs/label/2004/18887slr020_intal_lbl.pdf.
Palacios et al., "The pharmacological assessment of RS 86 (2-ethyl-8-methyl-2,8-diazaspiro-[4,5]-decan-1,3-dion hydrobromide). A potent, specific muscarinic acetylcholine receptor agonist," Eur J Pharmacol, 125(1):45-62 (1986).
Panza et al., "Emerging drugs to reduce abnormal [beta]-amyloid protein in Alzheimer's disease patients," Expert Opin Emerging Drugs, 21(4): 377-391 (2016).
Panza et al., "Immunotherapy for Alzheimer's Disease: From anti-β-amyloid to tau-based Immunization strategies," Immunotherapy, 4(2):213-238 (2012).

(56) References Cited

OTHER PUBLICATIONS

Parajuli et al., "CCL11 enhances excitotoxic neuronal death by producing reactive oxygen species in microglia," Glia, 63: 2274-2284 (2015).
Parameswaran et al., "Tumor necrosis factor-α signaling in macrophages," Crit Rev Eukaryot Gene Expr, 20(2): 87-103 (2010).
Parepally et al., "Brain uptake of nonsteroidal anti-inflammatory drugs: ibuprofen, flurbiprofen, and indomethacin," Pharm Res, 23(5):873-881 (2006).
Park, J.H. et al., "Pathogenesis of cerebral microbleeds: In vivo imaging of amyloid and subcortical ischemic small vessel disease in 226 individuals with cognitive impairment". *Ann. Neurol.* (2013) 73, 584-593.
Parrella, E. et al., "The Role of Mast Cells in Stroke," *Cells* 8.5 (2019), 437 (22 pages).
Partial European Search Report for EP Application No. 19786110.7 dated Dec. 2, 2021.
Partial European Search Report for EP Application No. 19857627.4 dated May 2, 2022.
Partial European Search Report for EP Application No. 19895399.4 dated Jul. 26, 2022.
Pasqualetti et al., "The Role of Neuroinflammation in Dementias" Current Neurology and Neuroscience, 15(4): 1-11 (2015).
Patkai, J. et al., "Deleterious effects of IL-9-activated mast cells and neuroprotection by antihistamine drugs in the developing mouse brain," *Pediatr. Res.* (2001) 50, 222-230.
Petersen et al., "Neuropathologic features of amnestic mild cognitive impairment," Arch. Neurol. (2006) 63 (5): 665-672.
Petersen et al., "Vitamin E and donepezil for the treatment of mild cognitive impairment," N Engl J Med, 352(23):2379-2388 (2005).
Petersen R.C., "The Current Status of Mild Cognitive Impairment—What Do We Tell Our Patients?" Nat. Clin. Pract. Neurol., (2007) 3(2): 60-61.
Petersen, et al., "Mild cognitive impairment: clinical characterization and outcome," Arch. Neurol., (1999) 56 (3): 303-308.
Philips T. and Robberecht W. "Neuroinflammation in amyotrophic lateral sclerosis: role of glial activation in motor neuron disease". *Lancet Neurol.* (2011) 10(3):253-263.
Pluta, R. et al., "Brain ischemia activates β- and γ-secretase cleavage of amyloid precursor protein: significance in sporadic Alzheimer's disease," *Mol Neurobiol.* (2013) 47, 425-434.
Pratico, "Alzheimer's disease and non-steroidal anti-inflammatory drugs: Old therapeutic tools with novel mechanisms of action?" Current Medicinal Chemistry—Central Nervous System Agents 5(2):111-117 (2005).
Prins et al., "Treating Alzheimer's disease with monoclonal antibodies: current status and outlook for the future", *Alzheimer's research & therapy* 5.6: 1-6 (2013).
PubChem CID: 27503, "Cromolyn sodium", Created Jun. 24, 2005. Retreived from the Internet < URL: https://pubchem.ncbi.nlm.nih.gov/compound/Cromolyn-sodium>.
PubChem CID:204318, "Diethyl Cromoglycate," Created Aug. 9, 2005. Retrieved from the Internet <URL: https://pubchem.ncbi.nlm.nih.gov/compound/204318>.
Péhourcq et al., "Diffusion of arylpropionate non-steroidal anti-inflammatory drugs into the cerebrospinal fluid: a quantitative structure-activity relationship approach," Fundamental and Clinical Pharmacology, 18(1):65-70 (2004).
Radicava (edaravone) US Prescribing Information. Jersey City, New Jersey: MT Pharma America, Inc; May 2017.
Raivich, G. et al., "Neuroglial activation repertoire in the injured brain: graded response, molecular mechanisms and cues to physiological function". *Brain Res. Brain Res. Rev.* (1999) 30, 77-105.
Ramos et al., "Mast Cell Stabilization Improves Survival by Preventing Apoptosis in Sepsis," The Journal of Immunology, 185: 709-716 (2010).
Reagan-Shaw et al., "Dose Translation from Animal to Human Studies Revisited," The FASEB, 22: 659-661 (2007).
Renton. A.E.et al., "State of play in amyotrophic lateral sclerosis genetics," *Nat. Neurosci.* (2014) 17:17-23.
Reverchon et al., "Production of Cromolyn Sodium Microparticles for Aerosol Delivery by Supercritical Assisted Atomization," AAPS PharmSciTech 8(4), Article 114 (2007).
Richards et al., "Absorption and disposition kinetics of cromolyn sodium and the influence of inhalation technique," J Pharmacol Exp Ther, 241(3):1028-1032 (1987).
Richards et al., "Neurodegenerative diseases have genetic hallmarks of autoinflammatory disease," Hum Mol Genet, 27(R2): R108-R118 (2018).
Rilutek (riluzole) Tablets: US prescribing information. Cary, NC, USA: Covis Pharmaceuticals, Inc; 1995. (Revised Apr. 2016).
Roberts et al., "Next Generation Pharmaceutical Impactor (A New Impactor for Pharmaceutical Inhaler Testing). Part I: Design," Journal of Aerosol Medicine, 16(3): 283-299 (2003).
Romanin. C., et al., "Immunologically activated chloride channels involved in degranulation of rat mucosal mast cells," *EMBO J.* (1991) 10(12):3603-3608.
Rosen et al., "Mutations in Cu/Zn superoxide dismutase gene are associated with familial amyotrophic lateral sclerosis," *Nature*, 362: 59-62 (1993).
Rothwell, N. et al., "The role of interleukin 1 in acute neurodegeneration and stroke: pathophysiological and therapeutic implications," *J Clin Invest* (1997) 100, 2648-2652.
Rousselet et al., "Mouse Model of Intraluminal MCAO: Cerebral Infarct Evaluation by Cresyl Violet Staining," J Vis Exp, 69:e4038 (2012).
Sabbagh et al., "Latrepirdine, a potential novel treatment for Alzheimer's disease and Huntington's chorea," Curr Opin Investig Drugs, 11(1): 80-91 (2010).
Saleh I.A. et al. Evaluation of humoral immune response in adaptive immunity in ALS patients during disease progression. *J Neuroimmunol.* (2009) 215:96-101.
Sandoval, K.E., and Witt, K.A., "Blood-brain barrier tight junction permeability and ischemic stroke". *Neurobiology of Disease* (2008) 32, 200-219.
Sawada et al., "Induction of functional interleukin-2 receptor in mouse microglia," J Neurochem, 64: 1973-1979 (1995).
Schilling, M. et al., "Microglial activation precedes and predominates over macrophage infiltration in transient focal cerebral ischemia: a study in green fluorescent protein transgenic bone marrow chimeric mice". *Exp Neurol* (2003) 183, 25-33.
Schnabel, J. "Early Results of Alzheimer's Passive Vaccine Trial Mixed," http://www.dana.org/News/Details.aspx?id=42815 printed Jan. 19, 2017, pp. 1-3 (2008).
Schneider et al., "Current Alzheimer's disease clinical trials: methods and placebo outcomes," Alzheimers Dement, 5(5):388-397 (2009).
Selkoe, D.J., "Alzheimer's disease: genes, proteins, and therapy," *Physiol Rev.* (2001) 81, 741-766.
Shah et al., "The role of fluorine in medicinal chemistry," J Enzyme Inhib Med Chem, 22(5): 527-540 (2007).
Shalash et al., "The Relationship Between the Permeability and the Performance of Carrier-Based Dry Powder Inhalation Mixtures: New Insights and Practical Guidance," AAPS PharmSciTech, 19(2): 912-922 (2017).
Sheng et al., "Tumor necrosis factor alpha upregulates human microglial cell production of interleukin-10 in vitro," Clin Diagn Lab Immunol, 2(5): 604-608 (1995).
Shin et al., "Interpretation of Animal Dose and Human Equivalent Dose for Drug Development," Journal of Korean Oriental Medicine, 31(3):1-7 (2010).
Shoup et al., "Evaluation of fluorinated cromolyn derivatives as potential therapeutics for Alzheimer's Disease," Journal of Alzheimer's Disease, 80(2): 775-786 (2021).
Shoup et al., "Fluorinated Cromolyn Derivatives for Potential Alzheimer's Disease Treatment," J Nucl Med 60, 114 (2019).
Shur et al., "From single excipients to dual excipient platforms in dry powder inhaler products," International Journal of Pharmaceutics, 514: 374-383 (2016).
Silverstein, F.S. et al., "Cytokines and perinatal brain injury". *Neurochem Int* (1997) 30, 375-383.
Sinniah et al., "The Anti-allergic Cromones: Past, Present, and Future," Front Pharmacol, 8:827 (10 pages) (2017).

(56) References Cited

OTHER PUBLICATIONS

Sousa et al., "Cellular and Molecular Characterization of Microglia: A Unique Immune Cell Population," Front Immunol, 8(198): 1-18 (2017).
Stages of ALS,ALS Association Texas Chapter, Retrieved online <https://www.alstexas.org/understanding-als/stages/>: 4 pages (2019).
Steckel et al., "In-situ-micronization of disodium cromoglycate for pulmonary delivery," European Journal of Pharmaceutics and Biopharmaceutics, 55: 173-180 (2003).
STN database CAS RN: 16110-51-3 (Nov. 16, 1984).
Strbian et al., "Cerebral mast cells regulate early ischemic brain swelling and neutrophil accumulation," *J. Cereb. Blood Flow Metab.* 26:605-612 (2006).
Strbian et al., "Mast Cell Stabilization Reduces Hemorrhage Formation and Mortality After Administration of Thrombolytics in Experimental Ischemic Stroke," Circulation, 116(4):411-418 (2007).
Strbian, D. et al., "An emerging role of mast cells in cerebral ischemia and hemorrhage," *Ann Med* (2009) 41, 438-450.
Strbian, D. et al., "Mast cell blocking reduces brain edema and hematoma vol. and improves outcome after experimental intracerebral hemorrhage," *J. Cereb. Blood Flow Metab.* (2007) 27, 795-802.
Strejan et al., "Suppression of chronic-relapsing experimental allergic encephalomyelitis in strain-13 guinea pigs by administration of liposome-associated myelin basic protein," J Neuroimmunol, 7(1):27-41 (1984).
Subramaniam et al., "Targeting Microglial Activation States as a Therapeutic Avenue in Parkinson's Disease," Front Aging Neurosci, 9(176): 1-18 (2017).
Sun et al., "Fluorinated molecules as drugs and imaging agents in the CNS," Curr Top Med Chem, 6(14): 1457-1464 (2006).
Sun et al., "Mast cells promote atherosclerosis by releasing proinflammatory cytokines," Nat Med, 13(6):719-724 (2007).
Sun et al., "Synthesis of scyllo-inositol derivatives and their effects on amyloid beta peptide aggregation," Bioorganic & Medicinal Chemistry 16:7177-7184 (2008).
Sun, J.H. et al., "Post-stroke cognitive impairment: epidemiology, mechanisms and management," *Ann Transl Med* (2014) 2(8): 80 (16 pages).
Sunderland et al., "Decreased beta-amyloid1-42 and increased tau levels in cerebrospinal fluid of patients with Alzheimer disease," JAMA. (2003) 289:2094-103.
Szabo, K. et al., "Hippocampal lesion patterns in acute posterior cerebral artery stroke: clinical and MRI findings," *Stroke* (2009) 40, 2042-2045.
Tabert, et al., "Neuropsychological prediction of conversion to Alzheimer disease in patients with mild cognitive impairment," Arch Gen Psychiatry. (2006) 63(8): 916-924.
Takano et al., "OSF4-J-2 Disodium cromoglicate inhibits gene expression of inflammation-related cytokines in lungs of septic mice," Journal of Pharmacological Sciences; Joint Symposium of the Japanese Society of Clinical Pharmacology and Therapeutics and The Japanese Pharmacological Society, 115(Supp.1): 102P (2011).
Tanaka, R. et al., "Migration of enhanced green fluorescent protein expressing bone marrow-derived microglia/macrophage into the mouse brain following permanent focal ischemia," *Neuroscience* (2003) 117, 531-539.
Taverni et al., "Donepezil medicated memory improvement in traumatic brain injury during post acute rehabilitation," Brain Inj, 12(1):77-80 (1998).
Thal et al., "A Randomized, Double-Blind, Study of Rofecoxib in Patients with Mild Cognitive Impairment," Neuropsychopharmacology (2005) 30: 1204-1215.
Thal et al., "Frontotemporal lobar degeneration FTLD-tau: Preclinical lesions, vascular and Alzheimer-related co-pathologies", J Neural Transm (Vienna), 122(7): 1007-1018 (2015).
Thériault et al., "The dynamics of monocytes and microglia in Alzheimer's disease," Alzheimer's Res Ther, 7:41 (10 pages) (2015).
Tiglutik (riluzole) oral suspension: US prescribing information. Berwyn, PA, USA: ITF Pharma, Inc; 1995 (Revised Sep. 2018).
Trias et al., "Phenotypic transition of microglia into astrocyte-like cells associated with disease onset in a model of inherited ALS," Front Cell Neurosci, 7: 274 (8 pages) (2013).
Trias, E., et al., "Significance of aberrant glial cell phenotypes in pathophysiology of amyotrophic lateral sclerosis," *Neurosci. Lett.* (2017) 636: 27-31.
Tronde et al., "Pulmonary absorption rate and bioavailability of drugs in vivo in rats: structure-absorption relationships and physicochemical profiling of inhaled drugs," J Pharm Sci, 92(6):1216-1233 (2003).
Upadhyaya, P. et al., "Therapy of Alzheimer's disease: An update," African Journal of Pharmacy and Pharmacology 4(6):408-421 (2010).
US FDA Guidance for Industry Suicidal Ideation and Behavior: Prospective Assessment of Occurrence in Clinical Trials (2012).
Veld et al., "Nonsteroidal antiinflammatory drugs and the risk of Alzheimer's disease," N Engl J Med, 345(21):1515-1521 (2001).
Vidgren et al., "Effect of powder inhaler design on drug deposition in the respiratory tract," International Journal of Pharmaceutics, 42: 211-216 (1988).
Vu et al., "Fluid-Based Biomarkers for Amyotrophic Lateral Sclerosis," *Neurotherapeutics*, 14: 119-134 (2017).
Wake et al., "Resting Microglia Directly Monitor the Functional State of Synapses In Vivo and Determine the Fate of Ischemic Terminals," J Neurosci, 29(13):3974-3980 (2009).
Waldemar G., "Recommendations for the Diagnosis and Management of Alzheimer's Disease and Other Disorders Associated with Dementia: EFNS Guideline," Eur J Neurol. (2007) 14(1): e1-26.
Walker et al., "Immune phenotypes of microglia in human neurodegenerative disease: challenges to detecting microglial polarization in human brains," Alzheimer's Res Ther, 7:56 (9 pages) (2015).
Wang et al. "Allopregnanolone reverses neurogenic and cognitive deficits in mouse model of Alzheimer's disease," PNAS, 107(14): 6498-6503 (2010).
Wang et al., "Pharmaceutical stabilization of mast cells attenuates experimental atherogenesis in low-density lipoprotein receptor-deficient mice," Atherosclerosis, 229: 304-309 (2013).
Wang et al., "Preventative effect of OMZ-SPT on lipopolysaccharide-induced acute lung injury and inflammation via nuclear factor-kappa B signaling in mice," Biochemical and Biophysical Research Communications, 485(2): 284-289 (2017).
Weggen et al., "A subset of NSAIDs lower amyloidogenic Aβ42 independently of cyclooxygenase activity," Nature, 414(6860):212-216 (2001).
Wen, Y. et al., "Increased beta-secretase activity and expression in rats following transient cerebral ischemia," *Brain Res.* (2004) 1009, 1-8.
Wettstein et al., "Clinical trials with the cholinergic drug RS 86 in Alzheimer's disease (AD) and senile dementia of the Alzheimer type (SDAT)," Psychopharmacology, 84(4):572-573 (1984).
Wikipedia, "Cromoglicic acid", Aug. 22, 2017 (Aug. 22, 2017), retrieved on Sep. 3, 2019 from https://en.wikipedia.org/w/index.php?title=Cromoglicic_acid&oldid=796733877.
Wikipedia, "Familial Amyloidosis, Finnish Type", Oct. 30, 2022, Retrieved online from "https://en.wikipedia.org/w/index.php?title=Familial_Amyloidosis,_Finnish_Type&oldid=1119142865".
Wikipedia, "Majority", Sep. 1, 2022, Retrieved online from "https://en.wikipedia.org/w/index.php?title=Majority&oldid=1107851583".
Wilcock et al., "Changing Perspective on the Role of Neuroinflammation in Alzheimer's Disease," Int J Alzheimers Dis, 2012: 495243 (7 pages) (2012).
Wilhelmsson et al., "Injury Leads to the Appearance of Cells with Characteristics of Both Microglia and Astrocytes in Mouse and Human Brain," Cereb Cortex, 27(6): 3360-3377 (2017).
Wisniewski et al., "Immunotherapeutic Approaches for Alzheimer's Disease," *Neuron*, 85(6): 1162-1176 (2015).
Xiao et al., "Design, synthesis, and structure-activity relationships of 2-benzylidene-1-indanone derivatives as anti-inflammatory agents for treatment of acute lung injury," Drug Design, Development and Therapy, 12: 887-899 (2018).

(56) References Cited

OTHER PUBLICATIONS

Yan et al., "Anti-inflammatory drug therapy alters β-amyloid processing and deposition in an animal model of Alzheimer's disease," J Neurosci, 23:7504-7509 (2003).
Yan, S.D. et al., "RAGE-Aβ interactions in the pathophysiology of Alzheimer's disease," *Restor Neurol Neurosci.* (1998) 12, 167-173.
Yang et al., "Increased levels of MIP-1α in CSF and serum of ALS," Acta Neurologica Scandinavica, 134(2): 94-100 (2016).
Yilmaz, G. et al., "Role of T lymphocytes and interferon-γ in ischemic stroke," *Circulation* (2006) 113, 2105-2112.
Yokota et al., "Roles of mast cells in the pathogenesis of inflammatory myopathy," *Arthritis Research Therapy*, 16(R72): 13 pages (2014).
Yoshikawa et al., "Severe acute respiratory syndrome (SARS) coronavirus-induced lung epithelial cytokines exacerbate SARS pathogenesis by modulating intrinsic functions of monocyte-derived macrophages and dendritic cells. Journal of virology," J Virol, 83(7): 3039-3048 (2009).
Young et al., "Lactose Composite Carriers for Respiratory Delivery," Pharmaceutical Research, 26(4): 802-810 (2008).
Zazgornik et al., "Citric acid inhibits growth of Helicobacter pylori in vitro: a new strategy for eradication," Wein Klin Wochenschr, 123: 38-40 (2011).
Zekry, D. et al., "The vascular lesions in vascular and mixed dementia: the weight of functional neuroanatomy," *Neurobiol Aging* (2003) 24, 213-219.
Zhang et al., "Mast cell tryptase induces microglia activation via protease-activated receptor 2 signaling," Cellular Physiology and Biochemistry, 29: 931-940 (2012).
Zhang et al., "Cromolyn Reduces Levels of the Alzheimer's Disease-Associated Amyloid β-Protein by Promoting Microglial Phagocytosis," Sci Rep, 8:1144 (9 pages) (2018).
Zhang, R. et al., "Evidence for systemic immune system alterations in sporadic amyotrophic lateral sclerosis (sALS)," *J Neuroimmunol.* (2005) 159(1-2): 215-224.
Zhang, S. et al., "Cerebral mast cells contribute to postoperative cognitive dysfunction by promoting blood brain barrier disruption," *Behavioural Brain Research* (2016) 298, 158-166.
Zhang, X. et al., "Activated brain mast cells contribute to postoperative cognitive dysfunction by evoking microglia activation and neuronal apoptosis," *Journal of Neuroinflammation* (2016) 13: 127 (15 pages).
Zhang, X. et al., "Cerebral mast cells participate in postoperative cognitive dysfunction by promoting astrocyte activation," *Cellular Physiology and Biochemistry* (2016) 40, 104-116.
Zhao et al., "Microglia-targeting nanotherapeutics for neurodegenerative diseases," APL Bioeng, 4:030902 (17 pages) (2020).
Zheng et al., "Cerebral Atheroschlerosis is Associated with Cystic Infarcts and Microinfarcts, but not Alzheimer Pathologic Changes," Stroke, 44(10): 2835-2841 (2013).
Zhou et al., "Drug-lactose binding aspects in adhesive mixtures: controlling performance in dry powder inhaler formulations by altering lactose carrier surfaces," Adv Drug Deliv Rev, 64(3):275-284 (2012).
Zhu et al., "Pharmacy," Fourth Military Medical University Press, 309, (2007).
Zlokovic, "Neurovascular pathways to neurodegeneration in Alzheimer's disease and other disorders," Nat Rev Neurosci, 12(12):723-738 (2011).
Aljuffali et al. "The codrug approach for facilitating drug delivery and bioactivity." Expert opinion on drug delivery 13.9 (2016): 1311-1325.
Anonymous, "NIH clinical trial shows Remdesivir accelerates recovery from advanced COVID-19." National Institutes of Health (Apr. 29, 2020). https://www.nih.gov/news-events/news-releases/nih-clinical-trial-shows-remdesivir-accelerates-recovery-advanced-covid-19.
Durdagi et al., "Screening of clinically approved and investigation drugs as potential inhibitors of COVID-19 main protease: a virtual drug repurposing study." ChemRxiv. 1-31 (2020).
Eisenberg et al., "The Amyloid State of Proteins in Human Diseases" Cell 148, Mar. 16, 2012, pp. 1188-1203.
Manuelidis et al.,"Transmissible encephalopathy agents," Virulence 1.2 (2010): 101-104.
Mondal et al., "Spindle cell variant of medullary carcinoma of thyroid with nodal metastasis: Cytodiagnosis and diagnostic dilemma" Thyroid Research and Practice, May-Aug. 2012, vol. 9, Issue 2, 60-63.
Rautio et al., "Prodrugs: design and clinical applications." Nature Reviews Drug Discovery 7 (2008): 255-270.
Teller et al. "Presence of soluble amyloid B-peptide precedes amyloid plaque formation in Down's syndrome" Nature Medicine, vol. 2, No. 1, Jan. 1996, 93-95.
Tsivgoulis et al., "Recent Advances in Primary and Secondary Prevention of Atherosclerotic Stroke," Journal of Stroke, 20.2 (2018): 145-166.
Xie et al., "Combination antiviral therapy with lopinavir/ritonavir, arbidol and interferon-α1b for COVID-19." Antiviral Therapy 25.4 (2020): 233-239.
Yoshimi et al., "Importance of Hydrolysis of Amino Acid Moiety in Water-Soluble Prodrugs of Disodium Cromoglycate for Increased Oral Bioavailability," Journal of Pharmacobio-Dynamics 15.7 (1992): 339-345.

CROMOLYN DERIVATIVES AND USES THEREOF

CROSS-REFERENCE TO RELATED APPLICATIONS

This application is a U.S. National Stage Application of International Application No. PCT/US21/65200, filed Dec. 27, 2021, which claims the benefit of priority to U.S. Provisional Patent Application No. 63/131,135, filed Dec. 28, 2020; the entire contents of each of which are incorporated herein by reference.

BACKGROUND OF THE INVENTION

Cromolyn, also referred to as cromoglicic acid, is traditionally described as a mast cell stabilizer since it works by preventing the release of mediators such as histamine and cytokines from mast cells thereby stabilizing inflammatory cells. Prevention of mediator release is thought to result from indirect blockade of the entry of calcium ions into the membrane of sensitized mast cells. Cromolyn has also been shown to inhibit the movement of other inflammatory cells such as neutrophils, eosinophils, and monocytes.

Cromolyn is commonly marketed as the sodium salt sodium cromoglicate or cromolyn sodium for the treatment of asthma and various allergies. Typically, cromolyn is administered as a nasal spray or as a nebulized solution with an inhaler. However, cromolyn is a highly polar molecule, and thus suffers from poor bioavailability even when administered by inhalation. Moreover, many patients (especially children and the elderly) find inhalers difficult to use, and poor inhalation technique can affect the amount of drug reaching the lungs and the response to therapy.

Therefore, there is a need for the development of orally available cromolyn analogs.

SUMMARY OF INVENTION

Provided herein are compounds, compositions and methods useful in the treatment and/or prevention of disease. In some embodiments, the methods comprise administering a compound disclosed herein or a pharmaceutically acceptable salt thereof. In certain embodiments, the methods further comprise administering a pharmaceutically acceptable carrier.

In one aspect, the compounds disclosed herein have a structure of Formula I

I

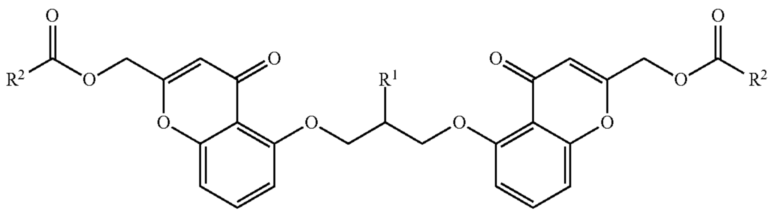

wherein $R^1$ is $OR^3$, $^{18}F$, or F;

$R^2$ is alkyl;

$R^3$ is H or acyl, or a pharmaceutically acceptable salt thereof.

In another aspect, provided herein is a method of treating or preventing a disease or condition comprising administering a compound having the structure of Formula I

I

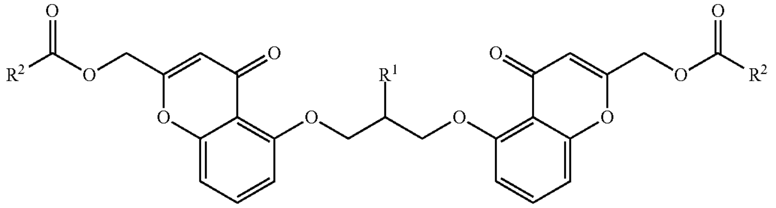

wherein $R^1$ is $OR^3$, $^{18}F$, orF $R^2$ is alkyl;

$R^3$ is H or acyl, or a pharmaceutically acceptable salt thereof, wherein the disease or condition is Alzheimer's disease, Huntington's disease, Parkinson's disease, amyotrophic lateral sclerosis, stroke, ischemic stroke, prion disease, a head injury, a traumatic brain injury, dementia, an infection, atherosclerosis, or asthma. In some embodiments, the method further comprises administering a pharmaceutically acceptable carrier. In some embodiments, the compound is administered orally. In certain embodiments, the compound is in a solid dosage form.

DETAILED DESCRIPTION

Figure 1:
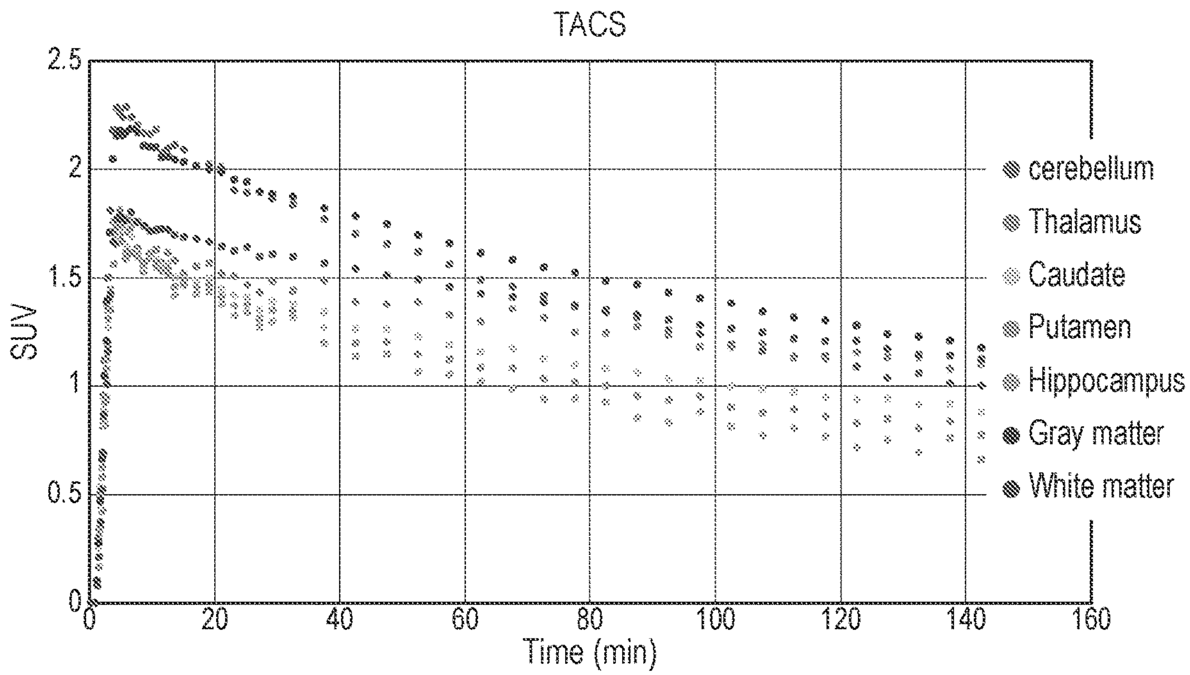
FIG. 1 is a plot showing the time activity curve (TAC) for a compound from a brain positron emission tomography (PET) imaging study.

In certain aspects, provided herein are cromolyn esters, compositions and methods related to the treatment and/or prevention of a disease or condition (e.g., Alzheimer's disease, Huntington's disease, Parkinson's disease, amyotrophic lateral sclerosis, stroke, ischemic stroke, prion disease, a head injury, a traumatic brain injury, dementia, an infection, atherosclerosis, asthma).

I. Compounds

In certain embodiments, provided herein are compounds having the structure of Formula I

I

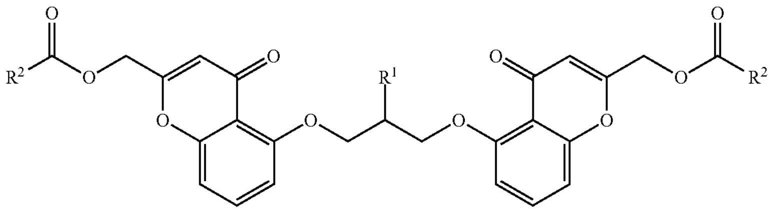

wherein $R^1$ is $OR^3$, $^{18}F$, or F;

$R^2$ is alkyl;

$R^3$ is H or acyl, or a pharmaceutically acceptable salt thereof. In some embodiments, $R^2$ is methyl or t-butyl. In some embodiments, $R^3$ is H or

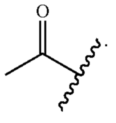

In certain embodiments, provided herein are compounds having the structure of Formula

I

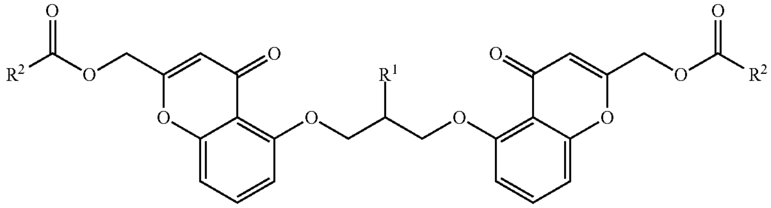

wherein $R^1$ is $OR^3$, $^{18}F$, or F;

$R^2$ is alkyl;

$R^3$ is H or acyl. In some embodiments, $R^2$ is methyl or t-butyl. In some embodiments, $R^3$ is H or

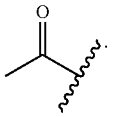

In certain embodiments, the compound is selected from the compounds identified in Table 1 or a pharmaceutically acceptable salt thereof. In certain embodiments, the compound is selected from the compounds identified in Table 1.

TABLE 1
| Compound | Structure |
|---|---|
| C7 | 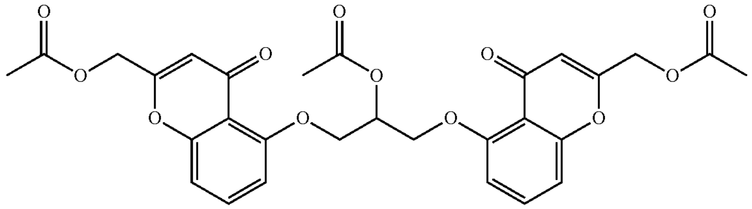 [SMILES: CC(=O)OCc1cc(=O)c2c(OCC(COc3cccc4oc(COC(C)=O)cc(=O)c34)OC(C)=O)cccc2o1] |
| C9 | 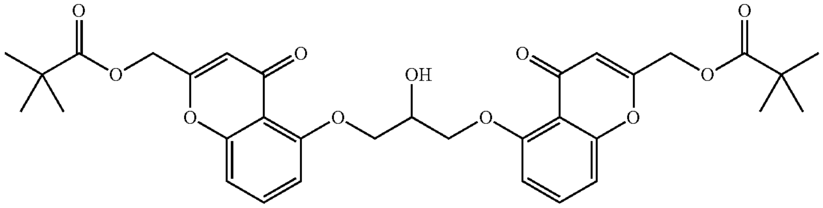 [SMILES: CC(C)(C)C(=O)OCc1cc(=O)c2c(OCC(O)COc3cccc4oc(COC(=O)C(C)(C)C)cc(=O)c34)cccc2o1] |
| C10 | 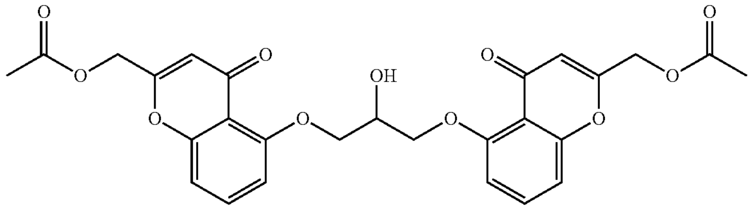 [SMILES: CC(=O)OCc1cc(=O)c2c(OCC(O)COc3cccc4oc(COC(C)=O)cc(=O)c34)cccc2o1] |
| C11 | 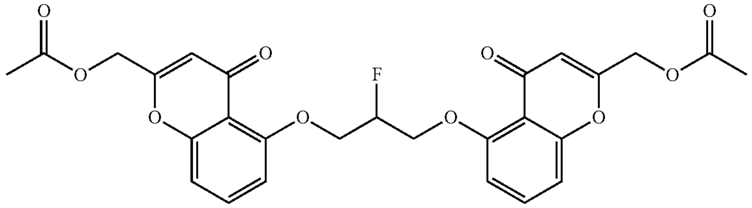 [SMILES: CC(=O)OCc1cc(=O)c2c(OCC(F)COc3cccc4oc(COC(C)=O)cc(=O)c34)cccc2o1] |
| C12 | 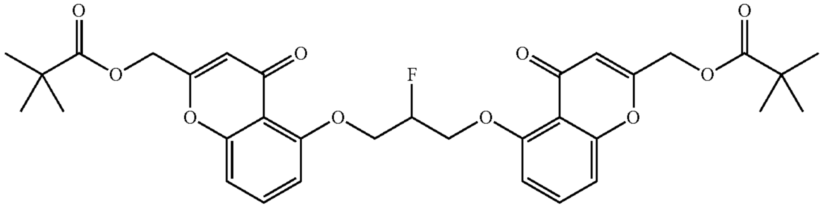 [SMILES: CC(C)(C)C(=O)OCc1cc(=O)c2c(OCC(F)COc3cccc4oc(COC(=O)C(C)(C)C)cc(=O)c34)cccc2o1] |
| C13 | 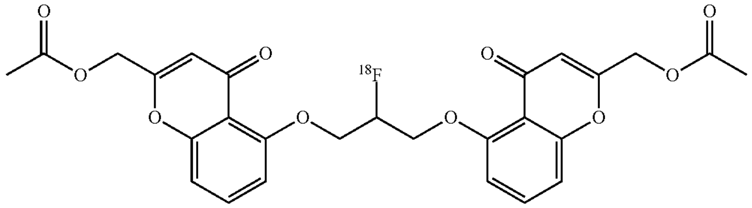 [SMILES: CC(=O)OCc1cc(=O)c2c(OCC([18F])COc3cccc4oc(COC(C)=O)cc(=O)c34)cccc2o1] |
| C14 | 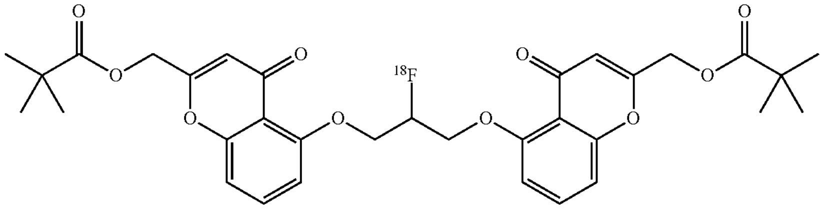 [SMILES: CC(C)(C)C(=O)OCc1cc(=O)c2c(OCC([18F])COc3cccc4oc(COC(=O)C(C)(C)C)cc(=O)c34)cccc2o1] |

In some embodiments, the compound is selected from the compounds identified in International application number PCT/US2017/049702, published as WO 2018/04517, which is expressly incorporated herein by reference in its entirety, and in particular regarding the compounds described therein.

II. Pharmaceutical Compositions

In certain embodiments, the present invention provides pharmaceutical compositions comprising a compound disclosed herein and a pharmaceutically acceptable carrier.

The compositions and methods of the present invention may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In a preferred embodiment, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as an eye drop.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a selfemulsifying drug delivery system or a selfmicroemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for rectal, vaginal, or urethral administration may be presented as a suppository, which may be prepared by mixing one or more active compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the pharmaceutical compositions for administration to the mouth may be presented as a mouthwash, or an oral spray, or an oral ointment.

Alternatively or additionally, compositions can be formulated for delivery via a catheter, stent, wire, or other intraluminal device. Delivery via such devices may be especially useful for delivery to the bladder, urethra, ureter, rectum, or intestine.

Formulations which are suitable for vaginal administration also include pessaries, tampons, creams, gels, pastes, foams or spray formulations containing such carriers as are known in the art to be appropriate.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention. Exemplary ophthalmic formulations are described in U.S. Publication Nos. 2005/0080056, 2005/0059744, 2005/0031697 and 2005/004074 and U.S. Pat. No. 6,583,124, the contents of which are incorporated herein by reference. If desired, liquid ophthalmic formulations have properties similar to that of lacrimal fluids, aqueous humor or vitreous humor or are compatable with such fluids. A preferred route of administration is local administration (e.g., topical administration, such as eye drops, or administration via an implant).

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion. Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinacious biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

An effective amount of the composition may be administered in a single dose per day or in fractional doses over the day, for example two to three times a day. By way of example, the administration of a composition according to the invention may be performed at a rate, for example, of 3 times a day or more, generally over a prolonged period of at least a week, 2 weeks, 3 weeks, 4 weeks, or even 4 to 15 weeks, optionally comprising one or more periods of stoppage or being repeated after a period of stoppage.

In certain embodiments, the compound may be administered at a dose between 1 mg and 1,500 mg per day, such as between 5 mg and 1,300 mg per day, such as between 10 mg and 900 mg per day, such as between 20 mg and 600 mg per day, such as between 40 mg and 300 mg per day, such as between 150 mg and 350 mg per day, such as between 40 and 150 mg per day, such as between 25 mg and 150 mg per day, such as between 2.5 mg and 150 mg per day, such as between 20 mg and 80 mg per day, or such as between 1 mg and 30 mg per day. In certain embodiments, the compound may be administered at a dose of 1,300 mg/day, 900 mg/day, 600 mg/day, 350 mg/day, 300 mg/day, 250 mg/day, 200 mg/day, 150 mg/day, 80 mg/day, 75 mg/day, 60 mg/day, 40 mg/day, 30 mg/day, 20 mg/day, 15 mg/day, 10 mg/day, 5 mg/day, or 2.5 mg/day.

Dosages for compounds may be as low as 5 ng/d. In certain embodiments, about 10 ng/day, about 15 ng/day, about 20 ng/day, about 25 ng/day, about 30 ng/day, about 35 ng/day, about 40 ng/day, about 45 ng/day, about 50 ng/day, about 60 ng/day, about 70 ng/day, about 80 ng/day, about 90 ng/day, about 100 ng/day, about 200 ng/day, about 300 ng/day, about 400 ng/day, about 500 ng/day, about 600 ng/day, about 700 ng/day, about 800 ng/day, about 900 ng/day, about 1 μg/day, about 2 μg/day, about 3 μg/day, about 4 μg/day, about 5 μg/day, about 10 μg/day, about 15 μg/day, about 20 μg/day, about 30 μg/day, about 40 μg/day, about 50 μg/day, about 60 μg/day, about 70 μg/day, about 80 μg/day, about 90 μg/day, about 100 μg/day, about 200 μg/day, about 300 μg/day, about 400 μg/day about 500 μg/day, about 600 μg/day, about 700 μg/day, about 800 μg/day, about 900 μg/day, about 1 mg/day, about 2 mg/day, about 3 mg/day, about 4 mg/day, about 5 mg/day, about 10 mg/day, about 15 mg/day, about 20 mg/day, about 30 mg/day, about 40 mg/day or about 50 mg/day of the compound is administered.

Dosage ranges for active agents may be from 5 ng/d to 100 mg/day. In certain embodiments, dosage ranges for active agents may be from about 5 ng/day to about 10 ng/day, about 15 ng/day, about 20 ng/day, about 25 ng/day, about 30 ng/day, about 35 ng/day, about 40 ng/day, about 45 ng/day, about 50 ng/day, about 60 ng/day, about 70 ng/day, about 80 ng/day, about 90 ng/day, about 100 ng/day, about 200 ng/day, about 300 ng/day, about 400 ng/day, about 500 ng/day, about 600 ng/day, about 700 ng/day, about 800 ng/day, or about 900 ng/day. In certain embodiments, dosage ranges for compounds may be from about 1 μg/day to about 2 μg/day, about 3 μg/day, about 4 μg/day, about 5 μg/day, about 10 μg/day, about 15 μg/day, about 20 μg/day, about 30 μg/day, about 40 μg/day, about 50 μg/day, about 60 μg/day, about 70 μg/day, about 80 μg/day, about 90 μg/day, about 100 μg/day, about 200 μg/day, about 300 μg/day, about 400 μg/day about 500 μg/day, about 600 μg/day, about 700 μg/day, about 800 μg/day, or about 900 μg/day. In certain embodiments, dosage ranges for active agents may be from about lmg/day to about 2 mg/day, about 3 mg/day, about 4 mg/day, about 5 mg/day, about 10 mg/day, about 15 mg/day, about 20 mg/day, about 30 mg/day, about 40 mg/day, about 50 mg/day, about 60 mg/day, about 70 mg/day, about 80 mg/day, about 90 mg/day, about 100 mg/day, about 200 mg/day, about 300 mg/day, about 400 mg/day, about 500 mg/day, about 600 mg/day, about 700 mg/day, about 800 mg/day, or about 900 mg/day.

In certain embodiments, the compounds are administered in pM or nM concentrations. In certain embodiments, the compounds are administered in about 1 pM, about 2 pM, about 3 pM, about 4 pM, about 5 pM, about 6 pM, about 7 pM, about 8 pM, about 9 pM, about 10 pM, about 20 pM, about 30 pM, about 40 pM, about 50 pM, about 60 pM, about 70 pM, about 80 pM, about 90 pM, about 100 pM, about 200 pM, about 300 pM, about 400 pM, about 500 pM, about 600 pM, about 700 pM, about 800 pM, about 900 pM, about 1 nM, about 2 nM, about 3 nM, about 4 nM, about 5 nM, about 6 nM, about 7 nM, about 8 nM, about 9 nM, about 10 nM, about 20 nM, about 30 nM, about 40 nM, about 50 nM, about 60 nM, about 70 nM, about 80 nM, about 90 nM, about 100 nM, about 300 nM, about 400 nM, about 500 nM, about 600 nM, about 700 nM, about 800 nM, or about 900 nM, concentrations.

This invention includes the use of pharmaceutically acceptable salts of compounds of the invention in the compositions and methods of the present invention. The term "pharmaceutically acceptable salt" as used herein includes salts derived from inorganic or organic acids including, for example, hydrochloric, hydrobromic, sulfuric, nitric, perchloric, phosphoric, formic, acetic, lactic, maleic, fumaric, succinic, tartaric, glycolic, salicylic, citric, methanesulfonic, benzenesulfonic, benzoic, malonic, trifluoroacetic, trichloroacetic, naphthalene-2-sulfonic, and other acids. Pharmaceutically acceptable salt forms can include forms wherein the ratio of molecules comprising the salt is not 1:1. For example, the salt may comprise more than one inorganic or organic acid molecule per molecule of base, such as two hydrochloric acid molecules per molecule of a compound. As another example, the salt may comprise less than one inorganic or organic acid molecule per molecule of base, such as two molecules of a compound per molecule of tartaric acid.

In certain embodiments, contemplated salts of the invention include, but are not limited to, L-arginine, benenthamine, benzathine, betaine, calcium hydroxide, choline, deanol, diethanolamine, diethylamine, 2-(diethylamino) ethanol, ethanolamine, ethylenediamine, N-methylglucamine, hydrabamine, 1H-imidazole, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn or other metal salts. In further embodiments, contemplated salts of the invention include, but are not limited to, alkyl, dialkyl, trialkyl or tetra-alkyl ammonium salts.

The pharmaceutically acceptable salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

As one of skill in the art will appreciate, compositions of the present invention, not having adverse effects upon administration to a subject, may be administered daily to the subject.

Preferred embodiments of this invention are described herein. Of course, variations, changes, modifications and substitution of equivalents of those preferred embodiments will become apparent to those of ordinary skill in the art upon reading the foregoing description. The inventors expect skilled artisans to employ such variations, changes, modifications and substitution of equivalents as appropriate, and the inventors intend for the invention to be practiced otherwise than specifically described herein. Those of skill in the art will readily recognize a variety of non-critical parameters that could be changed, altered or modified to yield essentially similar results. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

While each of the elements of the present invention is described herein as containing multiple embodiments, it should be understood that, unless indicated otherwise, each of the embodiments of a given element of the present invention is capable of being used with each of the embodiments of the other elements of the present invention and each such use is intended to form a distinct embodiment of the present invention.

III. Methods

In some embodiments, provided herein is a method for treating a disease or condition in a subject in need thereof, comprising administering to the subject a compound (e.g., a compound of Formula I) or a composition disclosed herein.

In some embodiments, the disease or condition is selected from Alzheimer's disease (AD), amyotrophic lateral sclerosis (ALS), stroke, ischemic stroke, prion disease, Huntington's disease, Parkinson's disease, head injury, traumatic brain injury (TBI), dementia, infection, atherosclerosis, asthma, and amyloidosis-associated condition.

An "amyloidosis-associated condition" is a disease that is associated with amyloid deposition and can include but not be limited to Alzheimer's Disease, idiopathetic myeloma, amyloid polyneuropathy, amyloid cardiomyopathy, systemic senile amyloidosis, amyloid polyneuropathy, hereditary cerebral hemorrhage with amyloidosis, Down's syndrome, Scrapie, medullary carcinoma of the thyroid, isolated atrial amyloid, $^{\beta}{}_2$-microglobulin amyloid in dialysis patients, inclusion body myositis, $\beta_2$-amyloid deposits in muscle wasting disease, and Islets of Langerhans diabetes Type I1 insulinoma. Type 2 diabetes mellitus, hereditary cerebral hemorrhage amyloidosis (Dutch), amyloid A (reactive), secondary amyloidosis, familial Mediterranean fever, familial amyloid nephropathy with urticaria and deafness (Muckle-wells Syndrome), amyloid lambda L-chain or amyloid kappa L-chain (idiopathic, myeloma or macroglobulinemia-associated) A beta 2M (chronic hemodialysis), ATTR (familial amyloid polyneuropathy (Portuguese, Japanese, Swedish)), familial amyloid cardiomyopathy (Danish), isolated cardiac amyloid, systemic senile amyloidoses, AIAPP or amylin insulinoma, atrial naturetic factor (isolated atrial amyloid), procalcitonin (medullary carcinoma of the thyroid), gelsolin (familial amyloidosis (Finnish)), cystatin C (hereditary cerebral hemorrhage with amyloidosis (Icelandic)), AApo-A-1 (familial amyloidotic polyneuropathy-Iowa), AApo-A-II (accelerated senescence in mice), head injuries (traumatic brain injury), dementia, fibrinogen-associated amyloid; and Asor or Pr P-27 (scrapie, Creutzfeld Jacob disease, Gertsmann-Straussler-Scheinker syndrome, bovine spongiform encephalitis) or in cases of persons who are homozygous for the apolipoprotein E4 allele, and the condition associated with homozygosity for the apolipoprotein E4 allele or Huntington's disease.

"Amyloidosis" is a condition characterized by the accumulation of various insoluble, fibrillar proteins in the tissues of a patient. An amyloid deposit is formed by the aggregation of amyloid proteins, followed by the further combination of aggregates and/or amyloid proteins.

Many forms of amyloidosis exist, and the disease can be classified into four groups: primary amyloidosis, secondary amyloidosis, hereditary amyloidosis, and amyloidosis associated with normal aging. Primary amyloidosis (light chain amyloidosis) occurs with abnormalities of plasma cells, and some people with primary amyloidosis also have multiple myeloma (cancer of the plasma cells). Typical sites of amyloid buildup in primary amyloidosis are the heart, lungs, skin, tongue, thyroid gland, intestines, liver, kidneys, and blood vessels. Secondary amyloidosis may develop in response to various diseases that cause persistent infection or inflammation, such as tuberculosis, rheumatoid arthritis, and familial Mediterranean fever. Typical sites of amyloid buildup in secondary amyloidosis are the spleen, liver, kidneys, adrenal glands, and lymph nodes. Hereditary amyloidosis has been noted in some families, particularly those from Portugal, Sweden, and Japan. The amyloid-producing defect occurs because of mutations in specific proteins in the blood. Typical sites for amyloid buildup in hereditary amyloidosis are the nerves, heart, blood vessels, and kidneys.

IV. Definitions

For purposes of the present invention, the following definitions will be used (unless expressly stated otherwise):

The terms "a," "an," "the" and similar referents used in the context of describing the present invention are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any unclaimed element is essential to the practice of the invention.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A $C_1$-$C_6$ straight chained or branched alkyl group is also referred to as a "lower alkyl" group. An alkyl group with two open valences is sometimes referred to as an alkylene group, such as methylene, ethylene, propylene and the like.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "$C_{x-y}$" when used in conjunction with a chemical moiety, such as, acyl, acyloxy, alkyl, alkenyl, alkynyl, or alkoxy is meant to include groups that contain from x to y carbons in the chain. For example, the term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-tirfluoroethyl, etc. $C_0$ alkyl indicates a hydrogen where the group is in a terminal position, a bond if internal. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond respectively. As applied to heteroalkyls, "$C_{x-y}$" indicates that the group contains from x to y carbons and heteroatoms in the chain. As applied to carbocyclic structures, such as aryl and cycloalkyl groups, "$C_{x-y}$" indicates that the ring comprises x to y carbon atoms. As applied to heterocyclic structures, such as heteroaryl and heterocyclyl groups, "$C_{x-y}$" indicates that the ring contains from x to y carbons and heteroatoms. As applied to groups, such as aralkyl and heterocyclylalkyl groups, that have both ring and chain components, "$C_{x-y}$" indicates that the ring and the chain together contain from x to y carbon atoms and, as appropriate heteroatoms.

The term "alkylamino", as used herein, refers to an amino group substituted with at least one alkyl group.

The term "alkylthio", as used herein, refers to a thiol group substituted with an alkyl group and may be represented by the general formula alkylS—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide", as used herein, refers to a group

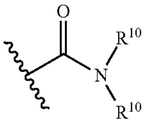

wherein each $R^{10}$ independently represent a hydrogen or hydrocarbyl group, or two $R^{10}$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

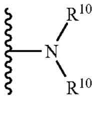

or

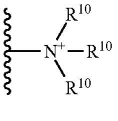

wherein each $R^{10}$ independently represents a hydrogen or a hydrocarbyl group, or two $R^{10}$ are taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

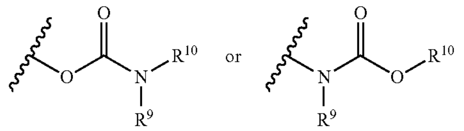

or wherein $R^9$ and $R^{10}$ independently represent hydrogen or a hydrocarbyl group, such as an alkyl group, or $R^9$ and $R^{10}$ taken together with the intervening atom(s) complete a heterocycle having from 4 to 8 atoms in the ring structure.

The terms "carbocycle", and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond. "Carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings. A "cycloalkenyl" group is a cyclic hydrocarbon containing one or more double bonds.

The term "carbocyclylalkyl", as used herein, refers to an alkyl group substituted with a carbocycle group.

The term "carbonate" is art-recognized and refers to a group $—OCO_2R^{10}$, wherein $R^{10}$ represents a hydrocarbyl group.

The term "carboxy", as used herein, refers to a group represented by the formula $—CO_2H$.

The term "ester", as used herein, refers to a group $—C(O)OR^{10}$ wherein $R^{10}$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The term "heteroalkyl", as used herein, refers to a saturated or unsaturated chain of carbon atoms and at least one heteroatom, wherein no two heteroatoms are adjacent. In analogy with alkyl groups, heteroalkyl groups with two open valences are sometimes referred to as heteroalkylene groups. Preferably, the heteroatoms in heteroalkyl groups are selected from O and N.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "heterocyclylalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocyclyl, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl sub stituent).

As used herein, "mitigating" means reducing the negative effects caused by exposure to ionizing radiation, relative to a cell, organ, tissue, or organism exposed to the same level of radiation for the same amount of time, but untreated.

As used herein, a "therapeutically effective amount" is an amount sufficient to mitigate the effects of the ionizing radiation.

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7. When a polycyclic substituent is attached through an aryl or heteroaryl ring, that sub stituent may be referred to herein as an aryl or heteroaryl group, while if the polycyclic substituent is attached through a cycloalkyl or heterocyclyl group, that substituent may be referred to herein as a cycloalkyl or heterocyclyl group. By way of example, a 1,2,3,4-tetrahydronaphthalen-1-yl group would be a cycloalkyl group, while a 1,2,3,4-tetrahydronaphthalen-5-yl group would be an aryl group.

The term "silyl" refers to a silicon moiety with three hydrocarbyl moieties attached thereto.

The term "substituted" refers to moieties having substituents replacing a hydrogen on one or more carbons or heteroatoms of the moiety. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds.

In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group $-OSO_3H$, or a pharmaceutically acceptable salt thereof.

The term "sulfonamide" is art-recognized and refers to the group represented by the general formulae

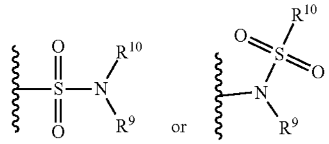

wherein $R^9$ and $R^{10}$ independently represents hydrogen or hydrocarbyl, such as alkyl, or $R^9$ and $R^{10}$ taken together with the intervening atom(s) complete a heterocycle having from 4 to 8 atoms in the ring structure.

The term "sulfoxide" is art-recognized and refers to the group $-S(O)-R^{10}$, wherein $R^{10}$ represents a hydrocarbyl.

The term "sulfonate" is art-recognized and refers to the group $SO_3H$, or a pharmaceutically acceptable salt thereof.

The term "sulfone" is art-recognized and refers to the group $-S(O)_2-R^{10}$, wherein $R^{10}$ represents a hydrocarbyl.

The term "thioalkyl", as used herein, refers to an alkyl group substituted with a thiol group.

The term "thioester", as used herein, refers to a group $-C(O)SR^{10}$ or $-SC(O)R^{10}$ wherein $R^{10}$ represents a hydrocarbyl.

The term "thioether", as used herein, is equivalent to an ether, wherein the oxygen is replaced with a sulfur.

The term "urea" is art-recognized and may be represented by the general formula

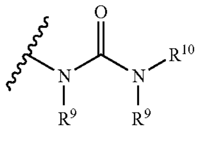

wherein $R^9$ and $R^{10}$ independently represent hydrogen or a hydrocarbyl, such as alkyl, or either occurrence of $R^9$ taken together with $R^{10}$ and the intervening atom(s) complete a heterocycle having from 4 to 8 atoms in the ring structure.

As used herein, the term “administering” means the actual physical introduction of a composition into or onto (as appropriate) a subject. Any and all methods of introducing the composition into subject are contemplated according to the invention; the method is not dependent on any particular means of introduction and is not to be so construed. Means of introduction are well known to those skilled in the art, and also are exemplified herein.

As used herein, the terms “effective amount”, “effective dose”, “sufficient amount”, “amount effective to”, “therapeutically effective amount” or grammatical equivalents thereof mean a dosage sufficient to produce a desired result, to ameliorate, or in some manner, reduce a symptom or stop or reverse progression of a condition and provide either a subjective relief of a symptom(s) or an objectively identifiable improvement as noted by a clinician or other qualified observer. Amelioration of a symptom of a particular condition by administration of a pharmaceutical composition described herein refers to any lessening, whether permanent or temporary, lasting, or transitory, that can be associated with the administration of the pharmaceutical composition.

As used herein, the term “pharmaceutically acceptable” refers to compositions that are physiologically tolerable and do not typically produce an allergic or similar untoward reaction when administered to a subject, preferably a human subject. Preferably, as used herein, the term “pharmaceutically acceptable” means approved by a regulatory agency of a federal or state government or listed in the U.S. Pharmacopeia or other generally recognized pharmacopeia for use in animals, and more particularly in humans.

As used herein, a therapeutic that “prevents” a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

A “subject,” as used herein, can be any mammal. For example, a subject can be a human, a non-human primate (e.g., monkey, baboon, or chimpanzee), a horse, a cow, a pig, a sheep, a goat, a dog, a cat, a rabbit, a guinea pig, a gerbil, a hamster, a rat, or a mouse. In some embodiments, the subject is an infant (e.g., a human infant). In some embodiments, the subject is a human.

The term “treating” is art-recognized and includes administration to the host of one or more of the subject compositions, e.g., to diminish, ameliorate, or stabilize the existing unwanted condition or side effects thereof.

EXEMPLIFICATION

The invention now being generally described, it will be more readily understood by reference to the following examples, which are included merely for purposes of illustration of certain aspects and embodiments of the present invention, and are not intended to limit the invention.

Example 1-Synthesis of Triacetate of 5,5'-[(2-hydroxy-1,3-propanediyl)bis(oxy)]bis[4-oxo-4H-1-benzopyran-2-ethanol

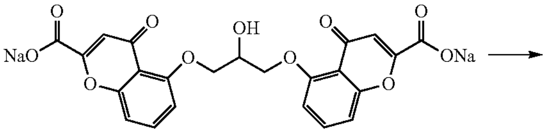

-continued

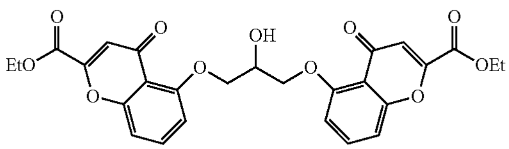

Briefly, a suspension of cromolyn sodium salt (1.0 g, 2 mmol) in EtOH (100 mL) and con. HCl (1 mL) was heated in a sealed reactor tube for 24 h at 100° C. The white solid was dissolved to give a clear colorless solution while hot. It was allowed to cool to room temperature and $NaHCO_3$ (1.0 g) was added. After stirring for 30 min at 25° C., solvent was removed by roto-evaporation. Chromatography on silica gel of the crude material using 5:95 methanol/methylene chloride yielded the diethyl ester (0.8 g, 76% yield); mp 154-156° C.; $^1$H NMR ($CDCl_3$, 300 MHz) σ 1.42 (t, 3H, J=7.1 Hz, $CH_3$), 2.73 (br s, 1H, OH), 4.44 (q, 4H, J=7.1 Hz, $2OCH_2CH_3$), 4.32-4.59 (m, 5H, CHOH, $2OCH_2$), 6.80 (s, 2H, 2vinyl-H), 6.99 (d, 2H, J=8.24 Hz, 2Aro-H), 7.12 (d, 2H, J=8.24 Hz, 2Aro-H), 7.17 (d, 2H, J=8.24 Hz, 2Aro-H), 7.71 (t, 2H, J=8.24 2Aro-H).

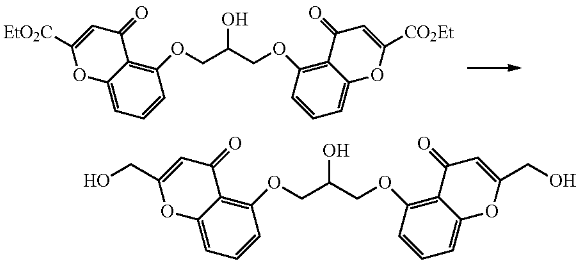

To a suspension of 5,5'-(2-hydroxytrimethylenedioxy)bis(4-oxochromene-2-carboxylic acid) diethyl ester (1.0 g, 1.86 mmol) in methanol (60 ml) and methylene chloride (40 mL) $NaBH_4$ (0.14 g, 3.72 mmol) was added in portions over a 1 h period. The mixture was stirred at 25° C. until it was clear (approx. 5 h) at which time the solution was quenched by dropwise addition of 1M HCl until acidic. Solvent was evaporated and the residue was extracted with methylene chloride. The combined organic extracts were washed with water and dried over anhydrous sodium sulfate. After evaporation, the residue was purified by column chromatography (5:95 methanol/methylene chloride) to yield 0.5 g (50%) of the triol; mp: 190-196° C.; $^1$H NMR (DMSO-$d_6$, 300 MHz) □ 2.73 (s, 3H, OH), 4.25-4.36 (m, 9H, 2OCH2, CH—O), 6.13 (s, 2H, 2 vinyl H), 7.04 (d, 2H, J=8.4 Hz, aromatic H), 7.07 (d, 2H, J=8.4 Hz, aromatic H), 7.63 (t, 2H, J=8.2 Hz, aromatic H). $^{13}$C NMR (100.62 MHz): δ176.16, 166.90, 157.87, 157.55, 134.17, 114.12, 110.34, 108.93, 108.31, 90.31, 88.58, 59.40, 67.87, 59.40.+pESI HRMS: calcd for $C_{23}H_{20}FO_9$: 440.1107; found: 440.1175.

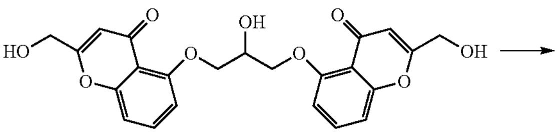

-continued

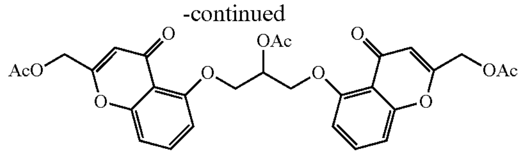

Acetic anhydride (0.5 g, 4.6 mmol)) was slowly added to a mixture of 5,5'-[(2-hydroxy-1,3-propanediyl)bis(oxy)]bis[4-oxo-4H-1-benzopyran-2-ethanol (0.5 g, 1.14 mmol) in pyridine (20 mL) cooled to 0-5° C. The mixture was stirred for 3 hr at 0-5° C. and then allowed to warm to room temperature. TLC indicted the reaction was complete. Methylene chloride was added and the mixture was washed with 10% HCl until the aqueous phase was acidic. The methylene chloride layer was dried over anhydrous sodium sulfate and solvent was evaporated. Chromatography on silica using 3% methanol in methylene chloride gave 0.45 g (72%) of the triacetate compound; mp 122-125° C.; $^{1}H$ NMR (CDCl3), δ 2.16 (s, 9 H, CH3), 4.58 (m, 2 H, CH2O), 4.66 (m, 2H, CH2O), 4.94 (s, 4 H, CH2O), 5.66 (m, 1 H, CH—O) 6.15 (s, 2H, 2vinyl-H), 6.94 (d, 2H, 2Aro-H), 6.97 (d, 2H, J=8.24 Hz, 2Aro-H), 7.52 (t, 2H, J=8.24, 2Aro-H). $^{13}C$ NMR (100.62 MHz): δ177.28, 170.83, 170.03, 160.10, 158.74, 158.14, 134.15, 115.01, 111.74, 110.46, 108.70, 70.09, 67.27, 61.55, 21.31, 20.79.+pESI HRMS: calcd for $C_{29}H_{26}O_{12}$; 566.1424; found: 566.1491.

Example 2-Synthesis of Diacetate of 5,5'-[(2-fluoro-1,3-propanediyl)bis(oxy)][4-oxo-4H-1-benzopyran-2-ethanol

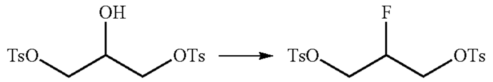 [SMILES: Cc1ccc(S(=O)(=O)OCC(O)COS(=O)(=O)c2ccc(C)cc2)cc1 ; Cc1ccc(S(=O)(=O)OCC(F)COS(=O)(=O)c2ccc(C)cc2)cc1]

A solution of 1,3-bis(4-methylbezenesulfonate propanetriol (2.7 g, 6.78 mmol) in methylene chloride (20 mL) at 0-5° C. was treated with DAST (2.18 g, 13.6 mmol). The mixture was stirred at 0-5° C. for 30 then allowed to warm to 25° C. and stirred for 16 hr. The mixture was poured into a sat'd sodium bicarbonate solution (30 mL) and layers separated. The methylene chloride layer dried (sodium sulfate). After solvent removal, the crude material was chromatographed on silica gel (methylene chloride) to yield 0.82 g (30%) of a solid; mp 99-102° C.; $^{1}H$ NMR ($CDCl_3$), δ 2.5 (s, 6H, $CH_3$), 4.15 (dd, 4H, J=12.3, 4.6 Hz,$CH_2$, 4.8 (dq, 1H, J=47, 4.6, CHF), 7.45 (d, 4H, J=8.1 Hz, Aro-H), 7.75 (d, 4H, J=8.4 Hz, Aro-H).

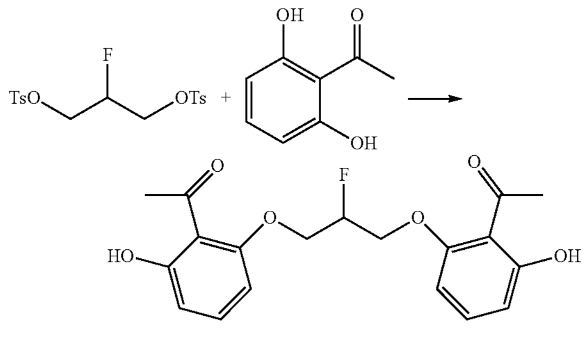

A mixture of 3-bis(4-methylbezenesulfonate)-2-fluoropropanediol (1.0, 2.5 mmol), 2,6-dihydroxyacetophenone (0.76 g, 5.0 mmol) and potassium carbonate (0.69 g) in acetonitrile (40 mL) was heated under reflux for 16 hr. The mixture was filtered and the filtrate was evaporated. The crude material was chromatographed on silica gel (acetonitrile/methylene chloride 5:95) to yield 0.57 g (40%) of product; mp 162-165° C.; $^{1}H$ NMR (d6-DMSO), δ 2.5 (s, 6H, $2CH_3$), 4.38 (m, 4H, $2CH_2$), 5.22 (br d 1H, J=49 Hz, CHF), 6.45 (m, 4H, 4Aro-H), 7.28 (t, 2H, J=4.55 Hz, 2Aro-H).

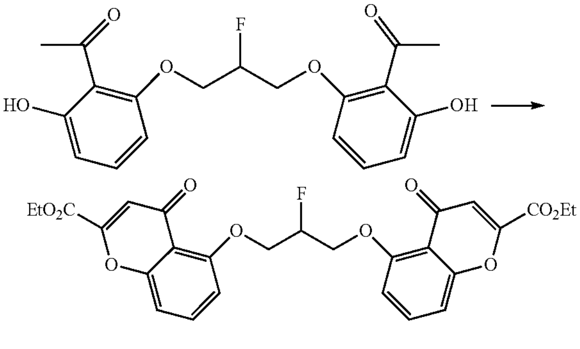

A mixture of 1,3-bis(2-acety-3-hydroxyphenoxy)-2-fluoropropane (200 mg, 0.52 mmol) and ethyl oxalate (2 mL) was added to a solution of sodium ethoxide (87 mg Na) in ethanol (10 mL) and benzene (10 mL). The mixture was heated at reflux for 16 hr, cooled and diluted with ether (50 mL). The precipitated sodium salt was filtered, washed with ether and dried. It was then dissolved in water and acidified with 10% HCl to obtain a sticky solid. The solid was refluxed in ethanol (20 mL) with a catalytic amount of 36% HCL for 1 hr. The mixture was poured into 50 mL of water and extracted twice with methylene chloride (50 mL). The extracts were combined and dried. After solvent removal, the crude material was chromatographed on silica gel (acetonitrile/methylene chloride 10:90) to yield 0.12 g (45%) of product; mp 166-170° C.; $^{1}H$ NMR ($CDCl_3$), δ 1.42 (t, 6H, J=7.14 Hz, $2CH_3$), 4.58 (q, 4H, J=7.14 Hz $2CH_2$), 4.65 (m, 4H, $2CH_2$), 5.35 (dq, 1H, J=46 Hz, J=4.4 HZ, CHF), 6.90 (s, 2H, vinyl-H), 6.95 (d, 2H, J=8.24 Hz, 2Aro-H), 7.13(d, 2H, J=8.24 Hz, 2Aro-H), 7.17 (d, 2H, J=8.24 Hz, 2Aro-H) 7.6 (t, 2H, J=8.24 2Aro-H).

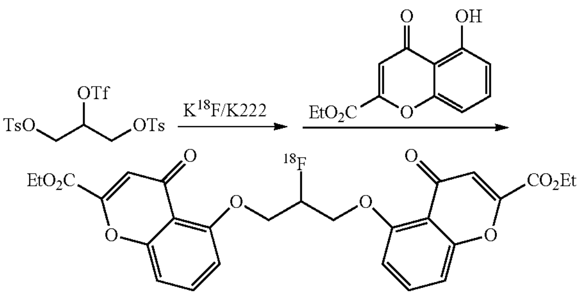

Alternatively, a solution of 1,3-bis[tolylsulfonyl)oxy]-2-[(trifluoromethyl)sulfonyl]oxy-propane (9 mg) in acetonitrile (0.4 mL) was added to a vial containing dried $K^{18}F$/Kryptofix complex (3 mg $K_2CO_3$, 7 mg Kryptofix) and fluorination was performed at 80° C. for 10 min. The resultant 2-[$^{18}F$]fluoropropane 1,3-ditosylate solution was passed through a silica gel SepPak using methylene chloride into a vial containing $K_2CO_3$ (10 mg) and ethyl 5-hydroxy-4-oxo-4H-chromene-2-carboxylate (10 mg). After solvent removal, DMSO was added and the mixture was heated for 10 min at 130° C. After addition of 1 mL of 5% HCl, followed by 2 mL of 50/50 acetonitrile 0.1 M ammonium formate and filtering (Millex-LCR 0.45 μm), F-18 cromolyn diester was purified by HPLC (C18, 50:50 acetonitrile/0.1 M ammonium formate). Synthesis was complete within 90 min with a yield of 20% (corrected for EOB) and chemical purity of greater than 95%.

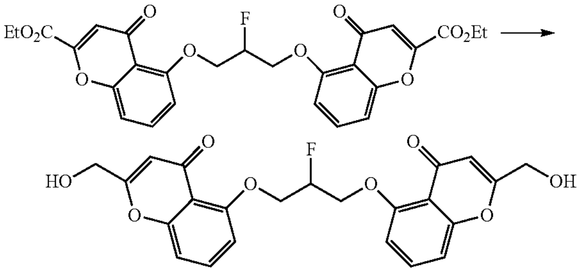

The above procedure for 5, 5'-(2-hydroxytrimethylenedioxy)bis(4-oxochromene-2-ethanol) was used. $^1$H NMR (DMSO-$d_6$, 300 MHz) δ 2.73 (s, 3H, OH), 4.25-4.36 (m, 8H, 2$OCH_2$, CH—O), 5.35 (br d, 1H, J=46 Hz, CHF), 6.13 (s, 2H, 2 vinyl H), 7.04 (d, 2H, J=8.4 Hz, aromatic H), 7.07 (d, 2H, J=8.4 Hz, aromatic H), 7.63 (t, 2H, J=8.2 Hz, aromatic H).

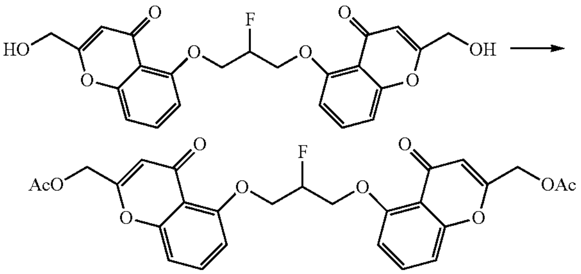

The above procedure for triacetate of 5,5'-[(2-hydroxy-1,3-propanediyl)bis(oxy)]bis[4-oxo-4H-1-benzopyran-2-ethanol was used. Chromatography on silica using 1% methanol in methylene chloride gave 0.41 g (70%) of the fluoro-diacetate compound; mp 125-126° C.; H1 NMR (CDCl3), δ 2.16 (s, 9 H, CH3), 4.58 (m, 2 H, CH2O), 4.66 (m, 2H, CH2O), 5.35 (br d, 1H, J=46 Hz, CHF); 6.15 (s, 2H, 2vinyl-H), 6.94 (d, 2H, 2Aro-H), 6.97 (d, 2H, J=8.24 Hz, 2Aro-H), 7.52 (t, 2H, J=8.24, 2Aro-H).

Example 3-Modulation of Aβ42 Uptake in Microglial Cells by Cromolyn Derivatives To test whether cromolyn derivatives impact Aβ42 uptake and clearance in BV2-CD33$^{WT}$ cells, BV2-CD33$^{WT}$ cells were treated with DMSO (control) or cromolyn derivatives at different concentrations ranging between 5 and 150 μM. The cromolyn derivatives assayed are summarized in Table 2.

TABLE 2

Summary of compounds tested in microglial cells

| Compound Number | Compound Name | |
|---|---|---|
| C1 | Cromolyn Disodium | 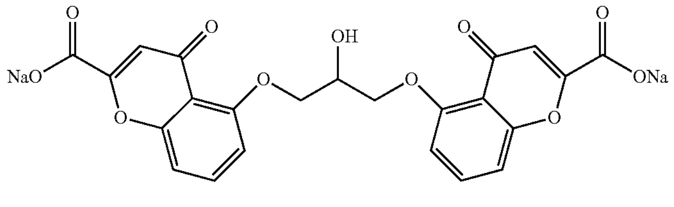 |
| C3 | ET-Cromolyn | 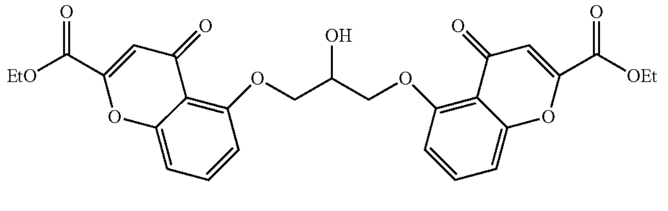 [SMILES: CCOC(=O)c1cc(=O)c2c(OCC(O)COc3cccc4oc(C(=O)OCC)cc(=O)c34)cccc2o1] |
| C4 | F-ET-Cromolyn | 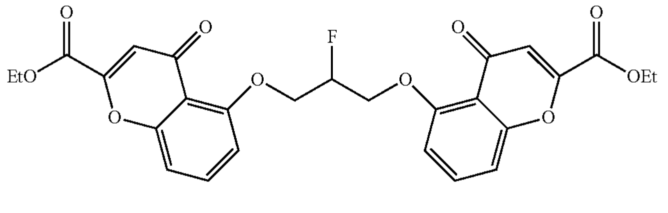 [SMILES: CCOC(=O)c1cc(=O)c2c(OCC(F)COc3cccc4oc(C(=O)OCC)cc(=O)c34)cccc2o1] |

TABLE 2-continued

| Summary of compounds tested in microglial cells | | |
|---|---|---|
| Compound Number | Compound Name | |
| C5 | Triol-Cromolyn | 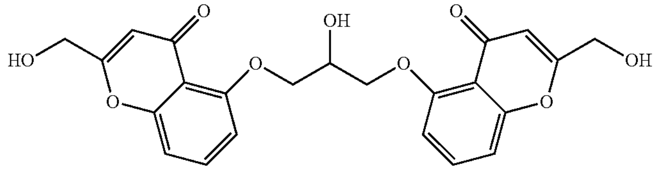 |
| C6 | F-Triol-Cromolyn | 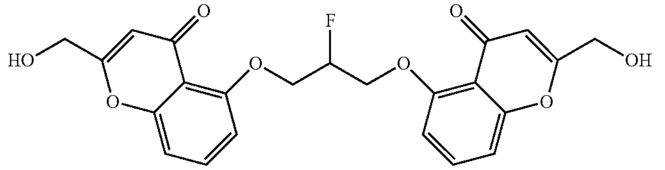 [SMILES: O=c1cc(CO)oc2cccc(OCC(F)COc3cccc4oc(CO)cc(=O)c34)c12] |
| C7 | Ac-Triol-Cromolyn | 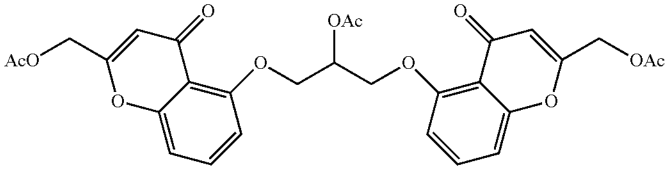 [SMILES: CC(=O)OCc1cc(=O)c2c(OCC(COc3cccc4oc(COC(C)=O)cc(=O)c34)OC(C)=O)cccc2o1] |
| C8 | POM-Cromolyn | 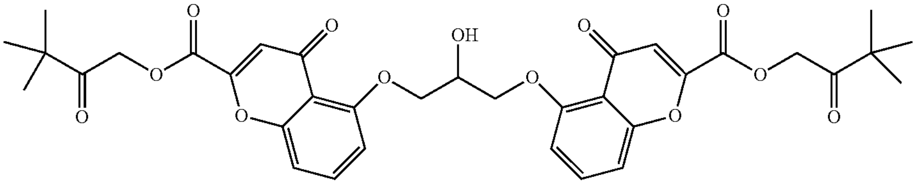 [SMILES: CC(C)(C)C(=O)COC(=O)c1cc(=O)c2c(OCC(O)COc3cccc4oc(C(=O)OCC(=O)C(C)(C)C)cc(=O)c34)cccc2o1] |

Figure 2:
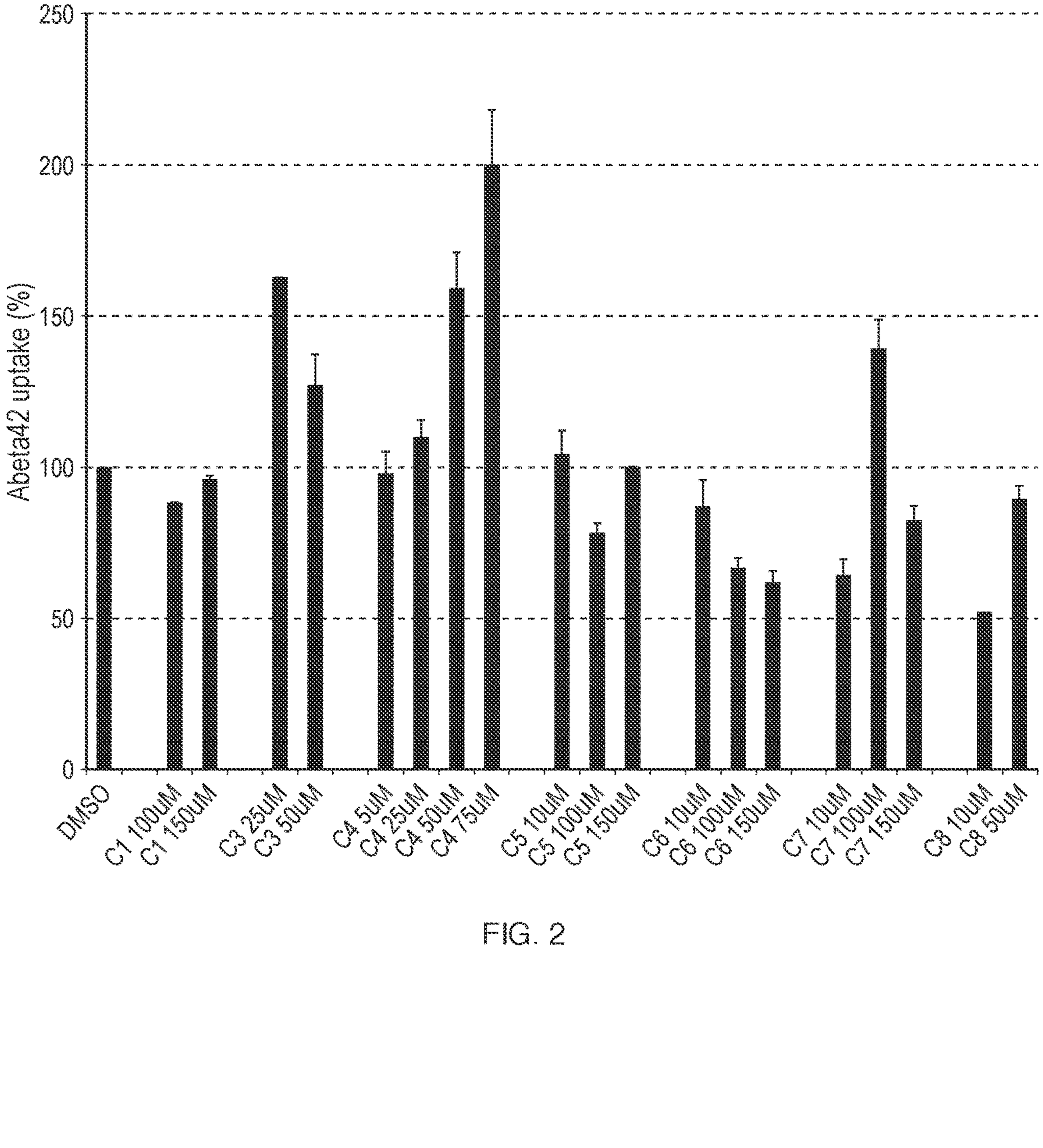
FIG. 2 is a plot showing Aβ42 uptake in microglial BV2-CD33$^{WT}$ cells treated with DMSO as control or cromolyn derivatives (C1, C3-8) at different concentrations for 3 hours. Afterwards, cells were incubated with DMSO or cromolyn derivatives in the presence of the Aβ42 peptide for additional 2 hours. Cell lysates were analyzed for intracellular levels of Aβ42 using an Aβ42-specific ELISA kit.

As shown in FIG. 2, C7 had a positive impact of microglial uptake of $A\beta_{42}$ in BV2-CD33 activated microglial cells at 100 μM. This increase microglial uptake of $A\beta_{42}$ may be due to the presence of acetyl groups on C7.

Incorporation by Reference

All publications and patents mentioned herein are hereby incorporated by reference in their entirety as if each individual publication or patent was specifically and individually indicated to be incorporated by reference. In case of conflict, the present application, including any definitions herein, will control.

Equivalents

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

What is claimed is:

1. A compound selected from

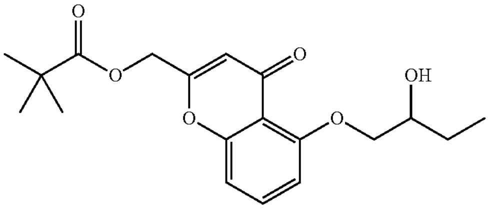

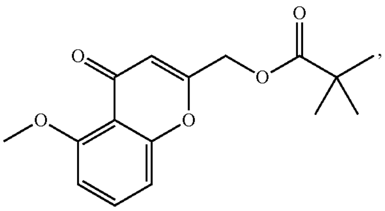
,

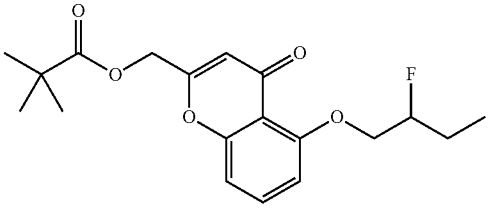

-continued
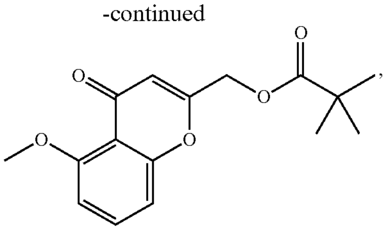
, and
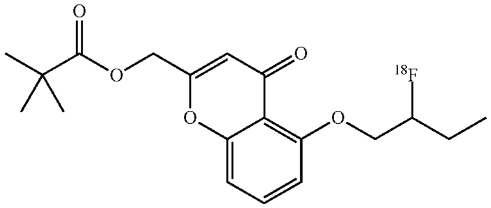
-continued
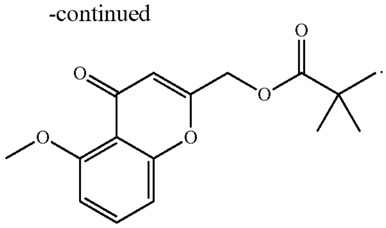
2. The compound of claim 1, having the following structure
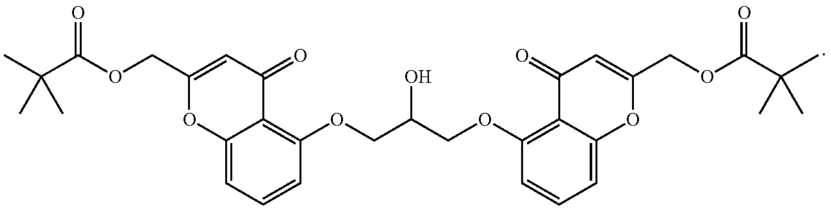 [SMILES: CC(C)(C)C(=O)OCc1cc(=O)c2c(OCC(O)COc3cccc4oc(COC(=O)C(C)(C)C)cc(=O)c34)cccc2o1]
3. The compound of claim 1, having the following structure
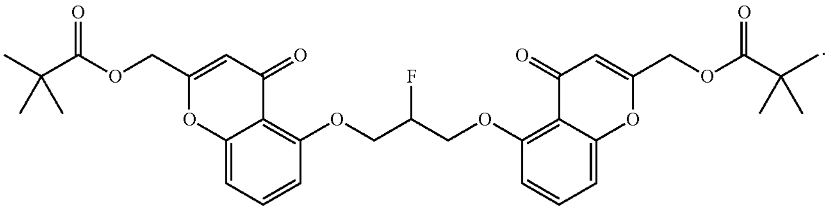 [SMILES: CC(C)(C)C(=O)OCc1cc(=O)c2c(OCC(F)COc3cccc4oc(COC(=O)C(C)(C)C)cc(=O)c34)cccc2o1]
4. The compound of claim 1, having the following structure
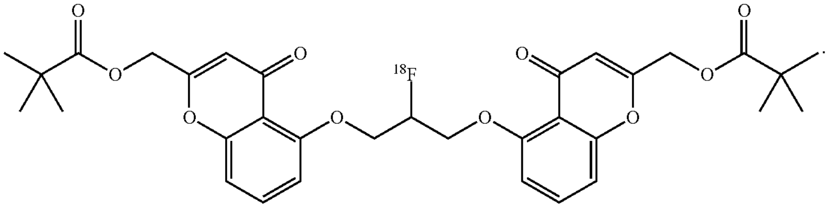 [SMILES: CC(C)(C)C(=O)OCc1cc(=O)c2c(OCC([18F])COc3cccc4oc(COC(=O)C(C)(C)C)cc(=O)c34)cccc2o1]

5. A pharmaceutical composition comprising a pharmaceutically acceptable carrier and a compound of claim 1.

6. A method of treating a disease or condition comprising administering a compound of claim 1 to a subject in need thereof, wherein the disease or condition is Alzheimer's disease, Huntington's disease, Parkinson's disease, amyotrophic lateral sclerosis, stroke, ischemic stroke, prion disease, a head injury, a traumatic brain injury, dementia, an infection, atherosclerosis, or asthma.

7. The method of claim 6, wherein the compound is administered orally.

8. The method of claim 6, wherein the compound is in a solid dosage form.

9. A method of imaging a disease or condition comprising administering a compound having the following structure

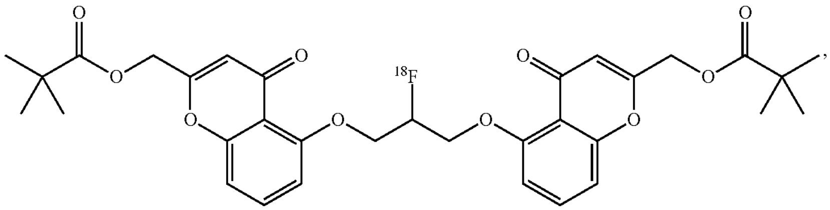 [SMILES: CC(C)(C)C(=O)OCc1cc(=O)c2c(OCC([18F])COc3cccc4oc(COC(=O)C(C)(C)C)cc(=O)c34)cccc2o1], wherein the disease or condition is Alzheimer's disease, Huntington's disease, Parkinson's disease, amyotrophic lateral sclerosis, stroke, ischemic stroke, prion disease, a head injury, a traumatic brain injury, dementia, an infection, atherosclerosis, or asthma.

10. The method of claim 9, wherein the compound is administered orally.

11. The method of claim 9, wherein the compound is in a solid dosage form.

12. A method of treating a disease or condition in a subject in need thereof comprising administering a compound selected from

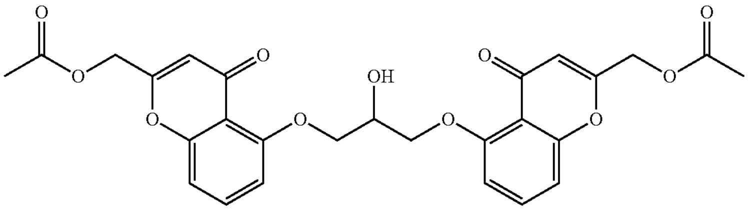,

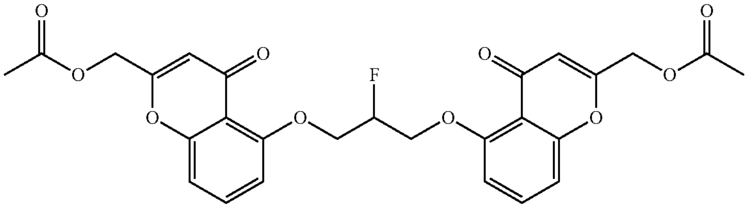,

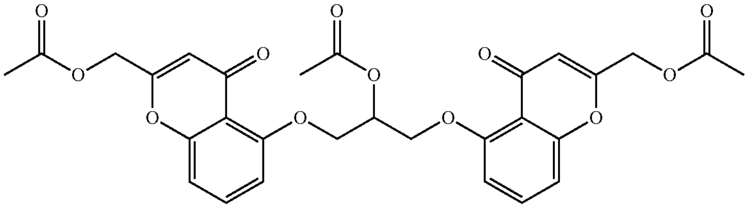, and

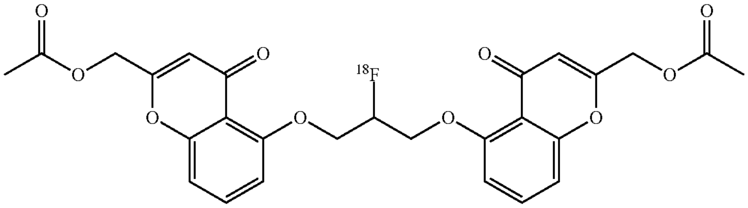, wherein the disease or condition is a head injury, a traumatic brain injury, atherosclerosis, or asthma.

13. The method of claim 12, wherein the compound is administered orally.

14. The method of claim 12, wherein the compound is in a solid dosage form.

15. The method of claim 12, wherein the compound is

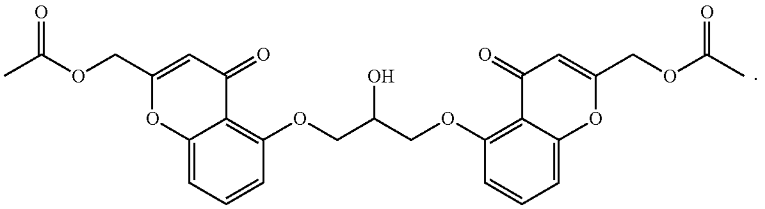 [SMILES: CC(=O)OCc1cc(=O)c2c(OCC(O)COc3cccc4oc(COC(C)=O)cc(=O)c34)cccc2o1]

16. The method of claim 12, wherein the compound is

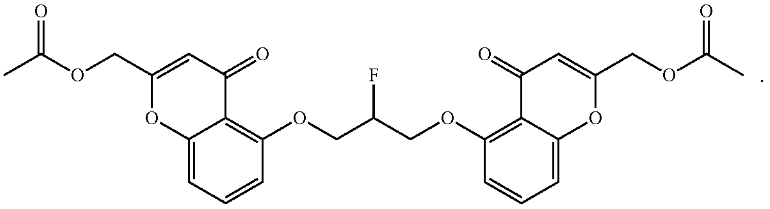 [SMILES: CC(=O)OCc1cc(=O)c2c(OCC(F)COc3cccc4oc(COC(C)=O)cc(=O)c34)cccc2o1]

17. The method of claim 12, wherein the compound is

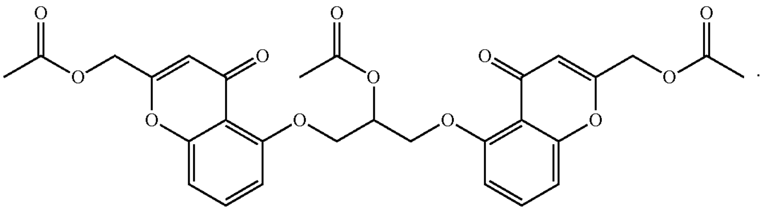 [SMILES: CC(=O)OCc1cc(=O)c2c(OCC(COc3cccc4oc(COC(C)=O)cc(=O)c34)OC(C)=O)cccc2o1]

18. The method of claim 12, wherein the compound is

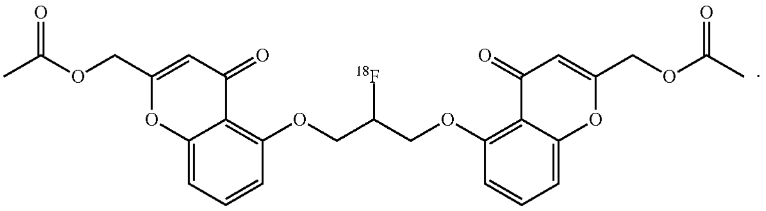 [SMILES: CC(=O)OCc1cc(=O)c2c(OCC([18F])COc3cccc4oc(COC(C)=O)cc(=O)c34)cccc2o1]

* * * * *